(12) United States Patent
Micklash, II et al.

(10) Patent No.: US 8,739,603 B2
(45) Date of Patent: Jun. 3, 2014

(54) APPARATUS FOR GAS SORPTION MEASUREMENT WITH INTEGRATED GAS COMPOSITION MEASUREMENT DEVICE AND GAS MIXING

(71) Applicant: Wildcat Discovery Technologies, Inc., San Diego, CA (US)

(72) Inventors: Kenneth James Micklash, II, Carmel, IN (US); Justin James Dutton, San Diego, CA (US); Steven Kaye, San Diego, CA (US)

(73) Assignee: Wildcat Discovery Technologies, Inc., San Diego, CA (US)

( * ) Notice: Subject to any disclaimer, the term of this patent is extended or adjusted under 35 U.S.C. 154(b) by 0 days.

(21) Appl. No.: 13/718,207

(22) Filed: Dec. 18, 2012

(65) Prior Publication Data

US 2013/0213117 A1 Aug. 22, 2013

Related U.S. Application Data

(60) Provisional application No. 61/601,699, filed on Feb. 22, 2012, provisional application No. 61/694,979, filed on Aug. 30, 2012.

(51) Int. Cl.
*G01N 7/00* (2006.01)

(52) U.S. Cl.
USPC ........................................................ 73/31.04

(58) Field of Classification Search
USPC ........................................................ 73/31.04
See application file for complete search history.

(56) References Cited

U.S. PATENT DOCUMENTS

| | | | | |
|---|---|---|---|---|
| 4,407,153 | A * | 10/1983 | Furlong et al. | 73/31.04 |
| 5,133,219 | A * | 7/1992 | Camp | 73/865.5 |
| 5,895,841 | A | 4/1999 | Lowell | |
| 6,306,349 | B1 | 10/2001 | Moon et al. | |
| 7,429,358 | B1 | 9/2008 | Gross | |
| 2002/0048536 | A1 | 4/2002 | Bergh et al. | |
| 2007/0157969 | A1 | 7/2007 | Gross | |
| 2009/0071235 | A1 | 3/2009 | Gross | |
| 2013/0137151 | A1* | 5/2013 | Tobey et al. | 435/161 |

OTHER PUBLICATIONS

PCT Search Report dated Apr. 19, 2013 for PCT application No. PCT/US2012/070291 filed Dec. 18, 2012.

* cited by examiner

*Primary Examiner* — Hezron E Williams
*Assistant Examiner* — Rodney T Frank
(74) *Attorney, Agent, or Firm* — Quinn Law Group, PLLC

(57) ABSTRACT

An apparatus for testing of multiple material samples includes a gas delivery control system operatively connectable to the multiple material samples and configured to provide gas to the multiple material samples. Both a gas composition measurement device and pressure measurement devices are included in the apparatus. The apparatus includes multiple selectively openable and closable valves and a series of conduits configured to selectively connect the multiple material samples individually to the gas composition device and the pressure measurement devices by operation of the valves. A mixing system is selectively connectable to the series of conduits and is operable to cause forced mixing of the gas within the series of conduits to achieve a predetermined uniformity of gas composition within the series of conduits and passages.

19 Claims, 12 Drawing Sheets

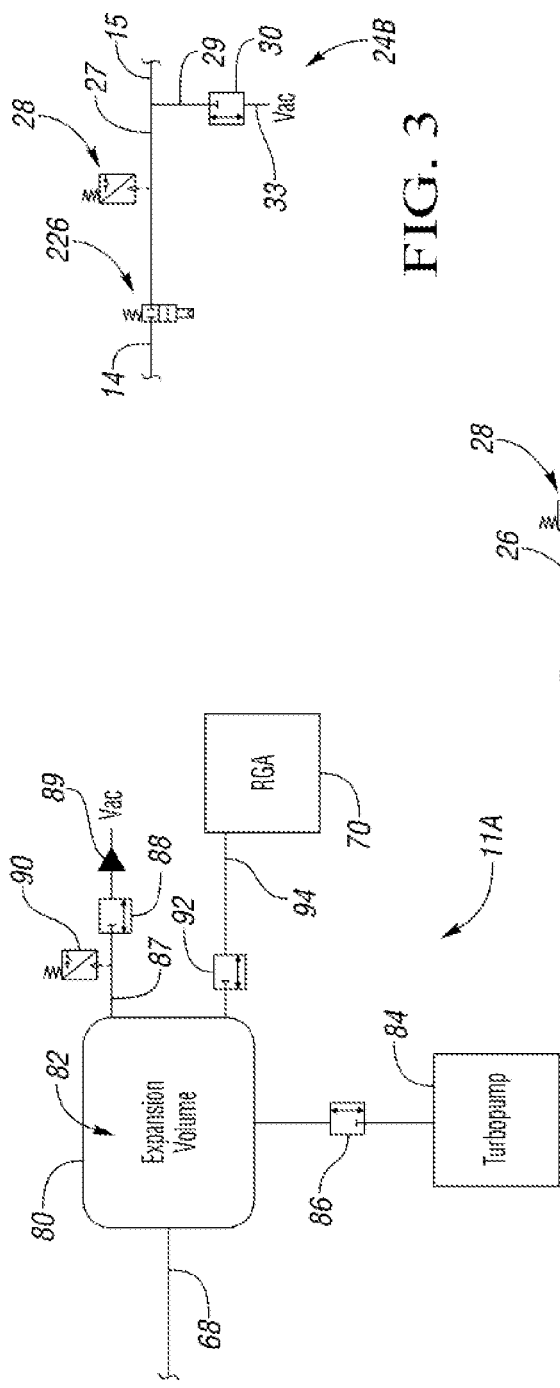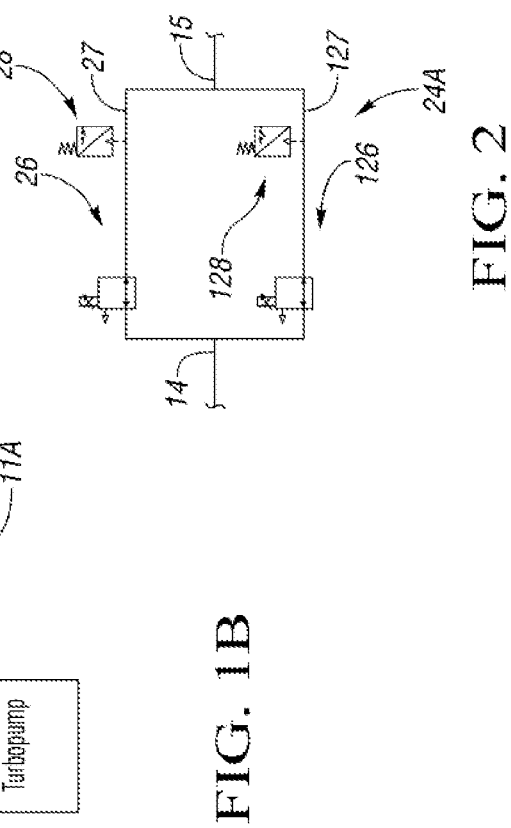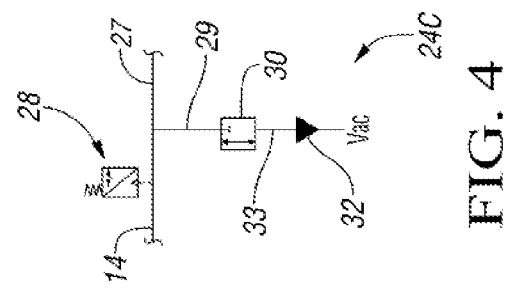
FIG. 1B
FIG. 2
FIG. 3
FIG. 4

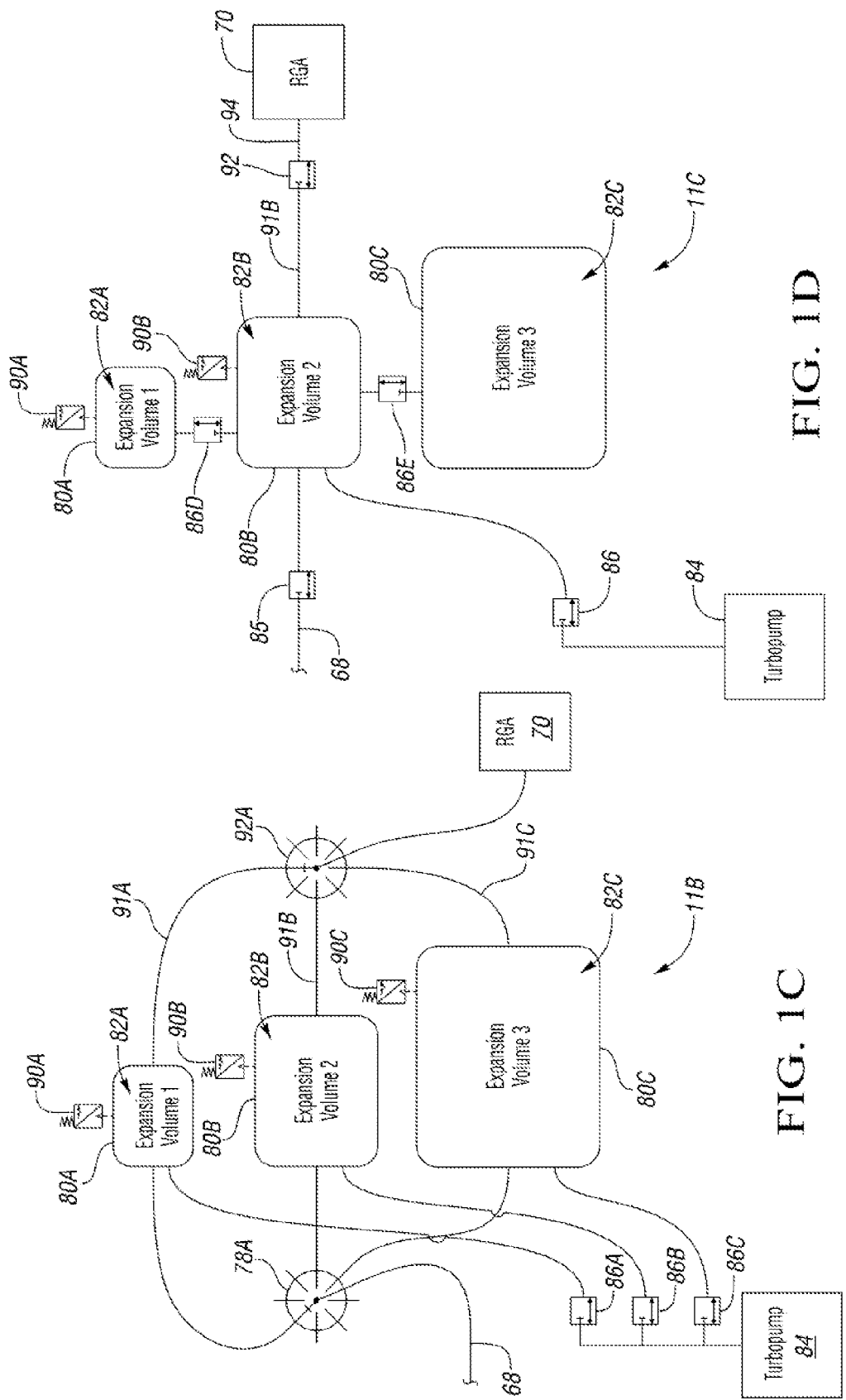

APPARATUS FOR GAS SORPTION MEASUREMENT WITH INTEGRATED GAS COMPOSITION MEASUREMENT DEVICE AND GAS MIXING

CROSS-REFERENCE TO RELATED APPLICATIONS

U.S. Provisional Application No. 61/601,699 filed on Feb. 22, 2012 is hereby incorporated by reference in its entirety. U.S. Provisional Application No. 61/694,979 filed on Aug. 30, 2012 is hereby incorporated by reference in its entirety.

STATEMENT REGARDING FEDERALLY-SPONSORED RESEARCH OR DEVELOPMENT

This invention was made with Government support under Award No. AR0000103, awarded by Advanced Research Projects Agency-Energy (ARPA-E), U.S. Department of Energy. The United States Government has certain rights in this invention.

TECHNICAL FIELD

The invention relates to an apparatus for testing gas sorption of material samples.

BACKGROUND

The success of high throughput testing of materials to identify composition and/or other properties of the materials is partially dependent on the reliability of the testing equipment, and the efficiency of the methods performed. Inherent limitations of the equipment used can directly limit the ability to explore a wide variety of materials. For example, the accuracy of some testing processes depends on the ability to accurately measure the amount of gas sorbed or released by the test material, as well as the type of gases sorbed when a multi-component test gas is used.

Gas sorption measurements are used for the testing of a material's ability to absorb/adsorb and reversibly desorb a gas. Common uses of such measurements are to determine the ability of a material to store hydrogen, carbon dioxide, nitrogen, or other gases. Traditional discovery techniques involve the sequential testing of materials, which is an inefficient and slow process. When using a multiple component gas, it is highly desirable to measure both the amount of gas taken up by the material as well as which gas was sorbed.

SUMMARY

In order to obtain accurate, high throughput gas sorption measurements while using a minimal amount of sample material, all component and line volumes through which the gas flows should be minimized. Diffusion of test gas through a test apparatus can thus be very slow, causing the gas composition in one part of the device nearest to the sample material to be different from the gas composition in the device further from the sample material. An apparatus for testing of multiple material samples is provided that overcomes this problem by integrating a mixing system within the apparatus. The mixing system can ensure a relatively uniform gas composition distributed throughout the various internal volumes of the testing apparatus.

Specifically, an apparatus for testing of multiple material samples includes a gas delivery control system operatively connectable to the multiple material samples and configured to provide gas to the multiple material samples. A gas composition measurement device and pressure measurement devices are included in the apparatus.

The apparatus includes multiple selectively openable and closable valves and a series of conduits configured to selectively connect the multiple material samples individually to the gas composition device and the pressure measurement devices by operation of the valves. The gas composition measurement device is downstream in the series of conduits from the multiple material samples and the pressure measurement devices. The gas composition measurement device determines the composition of gas in the series of conduits. The pressure measurement devices measure pressure of gas in the series of conduits for determining gas sorption by the multiple material samples.

A mixing system is selectively connectable to the series of conduits and is operable to cause forced mixing of the gas within the series of conduits for each of the multiple material samples. The mixing increases uniformity of gas distribution and gas composition within the series of conduits and passages so that gas delivered from the series of conduits to the gas composition measurement device is representative of gas composition after gas sorption by the material samples.

The gas composition measurement device is selectively operatively connected to each of the multiple material samples in parallel with the gas delivery control system and is operable to measure multiple component gases in fluid communication with the material samples after gas sorption by each of the multiple material samples. A pressure reduction system is configured to reduce gas pressure of gas provided from the multiple gas flow channels to the gas composition measurement device. In alternative embodiments, the gas pressure may not need to be reduced before sampling gas to the gas composition measurement device.

The gas composition measurement device may be a mass spectrometer. The apparatus allows gas sorption testing at a wide range of pressures from high levels of vacuum to several bar above atmospheric pressure (up to 6 bar in some embodiments). The mass spectrometer allows measurement of the makeup of multiple component gases after sorption, but is limited to a lower input pressure than that at which the sorption testing can occur. By ensuring that pressure is within the operating range of the mass spectrometer, the pressure reduction system allows the multiple material samples to be tested for gas sorption over the wide pressure and vacuum ranges, while allowing gas composition measurement to occur in parallel with a single mass spectrometer.

By integrating high throughput mass spectrometry with high throughput gas dosing and pressure measurement, the system is able to evaluate materials for a much more diverse array of properties than other high throughput sorption devices. Decomposition of the materials during the sorption process can also be determined. Applications for the tested materials can include gas storage, gas separation, gas purification, and gas phase catalysis.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 1B is a schematic illustration of a remainder of the device of FIG. 1A, showing a first embodiment of a pressure reduction system;

FIG. 1C is a schematic illustration of an alternate remainder of the device of FIG. 1A showing a second embodiment of a pressure reduction system;

FIG. 1D is a schematic illustration of an alternate remainder of the device of FIG. 1A showing a third embodiment of a pressure reduction system;

FIG. 2 is a second embodiment of a pressure control system for use in the multi-channel gas sorption device of FIG. 1A;

FIG. 3 is a third embodiment of a pressure control system for use in the multi-channel gas sorption device of FIG. 1A;

FIG. 4 is a fourth embodiment of a pressure control system for use in the multi-channel gas sorption device of FIG. 1A;

DETAILED DESCRIPTION

Figure 1A:
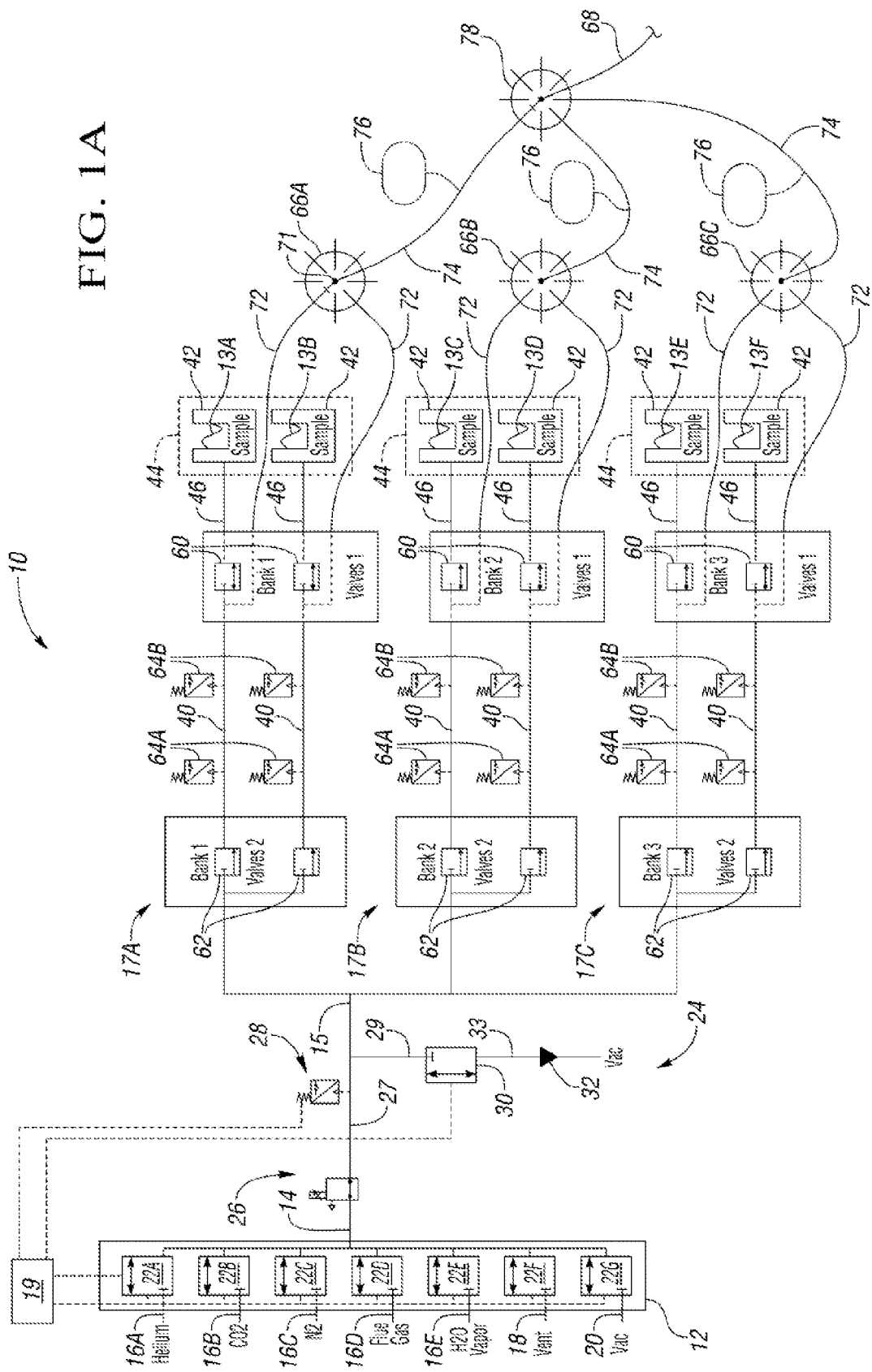
FIG. 1A is a schematic illustration of a portion of a first embodiment of a multi-channel gas sorption device including a first embodiment of a pressure control system.

Referring to the drawings, wherein like reference numbers refer to like components throughout the several views, FIG. 1A shows a schematic illustration of a portion of an apparatus referred to herein as a multi-channel gas sorption device 10. The remainder of the device 10 is a pressure reduction system 11A feeding a gas composition measurement device 70 shown in FIG. 1B, with alternate pressure reduction systems shown in FIGS. 1B-1H. The device 10 includes a delivery manifold 12 that connects multiple input gases to one common gas flow outlet 14 that feeds the remainder of the device 10 to allow gas sorption, mass spectrometry, and other measurements and evaluations of properties of multiple test materials 13A, 13B, 13C, 13D, 13E, and 13F, also referred to herein as material samples. Multiple test gas inputs 16A, 16B, 16C, 16D and 16E are connected to different gas sources. In this embodiment, the input test gases at gas inputs 16A, 16B, 16C, 16D and 16E are helium, carbon dioxide, nitrogen, flue gas, and water vapor, respectively, although different or additional gas sources may be used. A system vent 18 and system vacuum 20 are also connected to the delivery manifold 12. Flow from each gas input 16A-16E to the outlet 14, flow from between the vent 18 and the outlet 14, and flow between the vacuum 20 and the outlet 14 is controlled by a two-way, normally-closed solenoid valve 22A, 22B, 22C, 22D, 22E, 22F and 22G, respectively. Alternatively, the valves 22A-22G can be pneumatic valves. A controller 19 with a processor runs a stored algorithm that controls electronics to control opening of the valves 22A, 22B, 22C, 22D, 22E, 22F and 22G to: (i) permit the selected inlet gas to flow to the outlet 14; (ii) vent at least a portion of the device 10 through the vent 18; or (iii) apply the vacuum source 20 to at least a portion of the device 10 through the delivery manifold 12. The controller 19 is operatively connected to all valves within FIGS. 1A-1H and FIGS. 2-5, although the controller 19 is not shown in all of the Figures for purposes of clarity in the drawings. A person of ordinary skill in the art would understand how a controller can be operatively connected to each of the valves through conductive wires. Alternatively, pneumatic air lines can be used to control each of the valves.

The device 10 is configured to control a wide range of pressures (from vacuum to multiple bar in some embodiments). Accordingly, a very flexible yet precise pressure control of the device 10 is required. Any one of multiple embodiments of pressure control systems 24, 24A, 24B, 24C, 24D, shown in FIGS. 1A and 2-5, may be used for control of pressure at a common inlet 15 of channels 40 of valve banks 17A, 17B, 17C. As used herein, a "valve bank" is a structure supporting valves and forming channels between the valves. The delivery manifold 12, any of the pressure control systems 24, 24A, 24B, 24C and 24D as well as the channels 40 and valve banks 17A, 17B, 17C are referred to herein as a gas delivery control system.

In all embodiments, before an input test gas is delivered at the outlet 14, channels, secondary volumes, and delivery volumes of the device 10 are pulled to vacuum by opening valve 22G and/or by applying one or more vacuums at other portions of the device 10 to ensure that no residual gases remain in the device 10. Depending on the level of vacuum required, a turbopump may be used. In one exemplary embodiment, dose pressures of the test gas provided to the material samples 13A-13F may be between 15 mbar and 1300 mbar.

After channels, secondary volumes, and delivery volumes of the device 10 are at vacuum, one of the following five pressure control systems 24, 24A, 24B, 24C, 24D may be used. A first pressure control system 24 is shown in FIG. 1A. The pressure control system 24 includes a pressure regulator 26 that is tuned to allow accurate pressure delivery in a passage 27 to the inlet 15 at pressures above a predetermined pressure, such as pressure above one bar. A feedback pressure transducer 28 is used to measure system pressure and provide feedback to the regulator 26. A passage 29 is in communication with the passage 27, and a valve 30 is selectively openable via the controller 19 to put the passage 29 in fluid communication with a vacuum source through an aperture, also referred to as an orifice 32, in a distal portion 33 of the passage 29 downstream of the valve 30. When the valve 30 is opened, the passage 27 is connected to a vacuum source, which may be the same or a different vacuum source as that at the delivery manifold 12.

When pressures below one bar are required (vacuum pressures), the pressure regulator 26 delivers one bar pressure to the passage 27. The valve 30 is then opened which connects the passage 27 to the vacuum source. In order to ensure controllability, the orifice 32 is sized so that pressure is bled off very slowly by the vacuum source. The feedback pressure transducer 28 is used to monitor the pressure in the passage 27 while it is bled down. When the pressure in the passage 27 falls to a predetermined level, the valve 30 is closed. Alternatively, if desired, the pressure regulator 26 could be removed and the passage 27 could be pressurized to the feed gas tank pressure and then pressure in the passage 27 could be pulled down through the orifice 32.

FIG. 2 shows an alternative embodiment of a pressure control system 24A that may be used in the device 10 of FIG. 1A in place of the pressure control system 24. The pressure control system 24A utilizes a first pressure regulator 26 and first feedback pressure transducer 28 in fluid communication with a passage 27 (referred to herein as a first passage) and arranged in parallel with a second pressure regulator 126 and second feedback pressure transducer 128 in fluid communication with a second passage 127 between the outlet 14 and the inlet 15. The first pressure regulator 26 may be optimized for regulating flow at a first range of pressures, such as pressures above one bar, and the second pressure regulator 126 may be optimized for regulating flow at a second range of pressures different than the first range of pressures, such as vacuum pressures. When a mixed gas is fed through a small orifice, fractionation (gases of different masses passing through the orifice at different rates) can result in diminished accuracy of the representativeness of sample downstream of the orifice. The first pressure regulator 26 may be designed with apertures sized to avoid gas fractionation.

FIG. 3 shows an alternative embodiment of a pressure control system 24B that may be used in the device 10 of FIG. 1A in place of the pressure control system 24. The pressure control system 24B includes a pressure control valve 226 that is used to control pressure of the flow in the passage 27 over the entire range of target test gas pressures. The pressure control valve 226 is actuated using a pulse width modulation strategy. The pressure control valve 226 is opened and closed quickly, so that a small amount of gas is allowed downstream of the pressure control valve 226 during each cycle. A feedback pressure transducer 28 provides feedback to the control algorithm in the controller 19. Once the desired pressure is reached in the passage 27, the pressure control valve 226 is closed. The pulse width and duty cycle of the pressure control valve 226 can be modified to ensure maximum accuracy. If the desired pressure is overshot, vacuum can be applied by opening valve 22G in the delivery manifold 12. While the vacuum is applied, the pressure control valve 226 can be pulse width modulated to reduce the pressure in the passage 27 to the target level. Alternatively, a separate optional valve 30 can be provided to allow communication with a vacuum source from passage 29 to distal portion 33 to reduce pressure in passage 27 to the desired pressure level. The valve 30 can be a pulse width modulated valve or an on-off solenoid valve. Fractionation can be avoided when the valve 30 is a pulse width modulated valve that opens wide (i.e., without significantly restricting flow in the passage 27) to prevent fractionation.

FIG. 4 shows another alternative embodiment of a pressure control system 24C that may be used in the device 10 of FIG. 1A in place of the pressure control system 24. The pressure control system 24C does not require a pressure regulator valve or a pulse width modulated pressure control valve. Instead, the pressure control system 24C has only the feedback pressure transducer 28, the valve 30 and the aperture 32 in communication with a vacuum source, such as the vacuum source available at the delivery manifold 12, when the valve 30 is opened. If the pressure control system 24C is used, the inlet pressures of all of the gases entering the delivery manifold 12 are set above the maximum pressure that is required for any testing. The selected gas at its set pressure is allowed to enter the pressure control system 24C at the outlet 14 of the delivery manifold 12 by opening one of the respective valves 22A-22E. The valve 30 is then opened, connecting the passage 27 to the vacuum source. The falling pressure in the passage 27 is monitored by the pressure transducer 28. Once the pressure in passage 27 reaches the desired level, the valve 30 is then closed.

Figure 5:
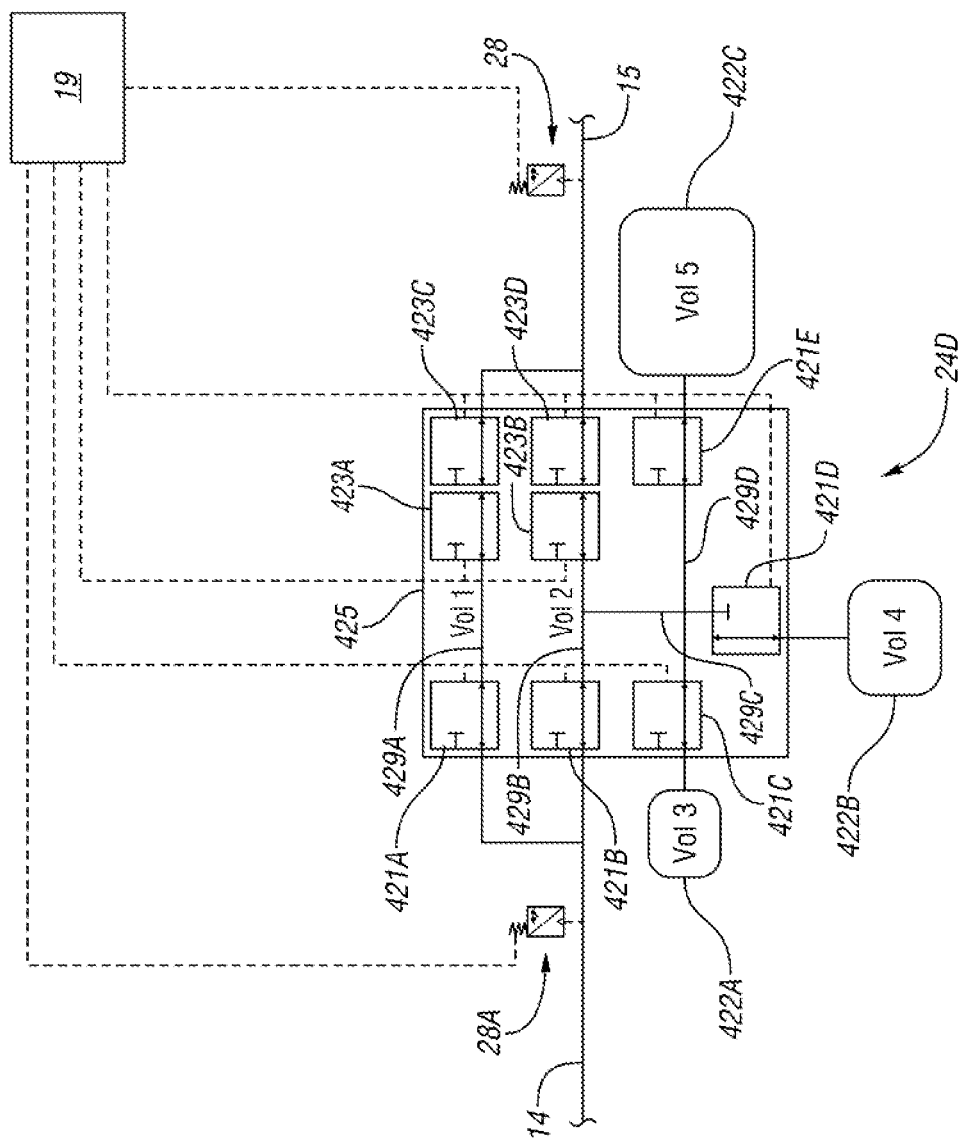
FIG. 5 is a fifth embodiment of a pressure control system for use in the multi-channel gas sorption device of FIG. 1A.

FIG. 5 shows another alternative embodiment of a pressure control system 24D that may be used in the device 10 of FIG. 1A in place of the pressure control system 24. The pressure control system 24D includes a dosing manifold 425 forming cavities and/or connectable to pressure vessels with cavities of different sized volumes by opening one or more selected inlet valves 421A, 421B, 421C, 421D, and 421E, and one of multiple outlet valves 423A and 423B. Outlet valves 423C and 423D are adjacent to outlet valves 423A and 423B, respectively. Outlet valves 423A and 423B hold differential pressure in one direction. They will hold pressure when in the closed position if pressure upstream of the valves 423A, 423B is greater than pressure at the inlet 15. Outlet valves 423C and 423D hold differential pressure in the opposite direction only. They will hold pressure in the closed position when the pressure at the inlet 15 is greater than the pressure upstream of the valves 423C, 423D. The valves 423A and 423C are controlled simultaneously. The valves 423B and 423D are controlled simultaneously. For purposes of illustration only, all of the valves in FIG. 5 except valve 421D are shown in an open position. The inlet valves 421A, 421B, 421C, 421D, and 421E are in selective fluid communication with the outlet 14 of the delivery manifold 12 of FIG. 1, and the outlet valves 423A and 423B are in selective fluid communication with the inlet 15 to the banks 17A, 17B, 17C of FIG. 1. In this embodiment, inlet valves 421A and 421B are in fluid communication with outlet 14 of delivery manifold 12. Inlet valves 421C, 421D and 421E are connected to outlet 14 through inlet valve 421B.

A first delivery volume Vol 1 is established in the manifold 425 in a passage 429A between the inlet valve 421A and the outlet valve 423A. A second delivery volume Vol 2 is established in the manifold 425 in a passage 429B between the inlet valve 421B and the outlet valve 423B, and includes the passages 429C and 429D extending to the inlet valves 421C, 421D, and 421E. A third delivery volume is established when inlet valves 421B and 421C are opened, as a volume Vol 3 of another cavity established by pressure vessel 422A that is normally closed off by inlet valve 421C is then added to delivery volume Vol 2. The third delivery volume is the total of Vol 2 and Vol 3. A fourth delivery volume is established when inlet valves 421B and 421D are opened, as a volume Vol 4 of another cavity established by pressure vessel 422B that is normally closed off by inlet valve 421D is then added to delivery volume Vol 2. The fourth delivery volume is the total of Vol 2 and Vol 4. A fifth delivery volume is established when inlet valves 421B and 421E are opened, as a volume Vol 5 of another cavity established by pressure vessel 422C that is normally closed off by inlet valve 421E is then added to delivery volume Vol 2. The fifth delivery volume is the total of Vol 2 and Vol 5. Other combinations of delivery volumes are also possible by opening selected combinations of the inlet valves 421A-421E. The passages 429A-429D are sized to avoid fractionation. This requires that the passages 429A-429D should be sized sufficiently larger than the mean free space of the sample gas. Additionally, in this embodiment, the gas is allowed sufficient time to equilibrate after expansion to ensure fractionation does not occur. The pressure control system 24D includes no apertures or restrictions that could cause fractionation. Furthermore, the selected inlet valves 421A-421E can remain open sufficiently long to ensure that fractionation cannot effect the test gas.

In the embodiment of FIG. 5, the pressures of all of the supply gases supplied through the delivery manifold 12 of FIG. 1A are set to a given pressure or pressures. By opening one or more of the desired inlet valves 421A, 421B, 421C, 421D, and 421E, a desired delivery pressure is then established as one or more of the particular volumes are filled with the selected supply gas. The inlet valves 421A, 421B, 421C, 421D, and 421E that were opened are then closed, and one or both outlet valves 423A, 423B are then opened, allowing the gas to expand downstream of the pressure control system 24D to establish a desired pressure at the inlet 15 of the valve banks 17A-17C. An algorithm stored in the controller 19 is used to determine which of the volumes Vol 1, Vol 2, Vol 3, Vol 4, Vol 5 are required to achieve a desired downstream system pressure, and controls the valves 421A, 421B, 421C, 421D and 421E accordingly. Information regarding supply gas pressure indicated by a pressure transducer 28A in fluid communication with the outlet 14, and the pressure at the inlet 15, as indicated by a feedback pressure transducer 28 in fluid communication with the inlet 15, is used by the controller 19 in determining which of the valves 421A, 421B, 421C, 421D and 421E to open to make any necessary adjustments to achieve the desired pressure at the inlet 15.

Referring again to FIG. 1A, the device 10 includes the multiple banks 17A, 17B, 17C each defining multiple parallel channels 40. The number of channels 40 per bank is equivalent to the number of sample vessels 42 contained in a material container assembly 44, discussed below. The total number of banks 17A, 17B, 17C is selected to ensure that the device 10 gives the desired number of parallel test channels 40. For purposes of clarity in the drawings, only three banks 17A, 17B, 17C with two channels 40 each are shown in FIG. 1A. However, the device 10 could have hundreds of banks to provide thousands of channels, enabling high throughput testing of thousands of material samples.

Figure 6:
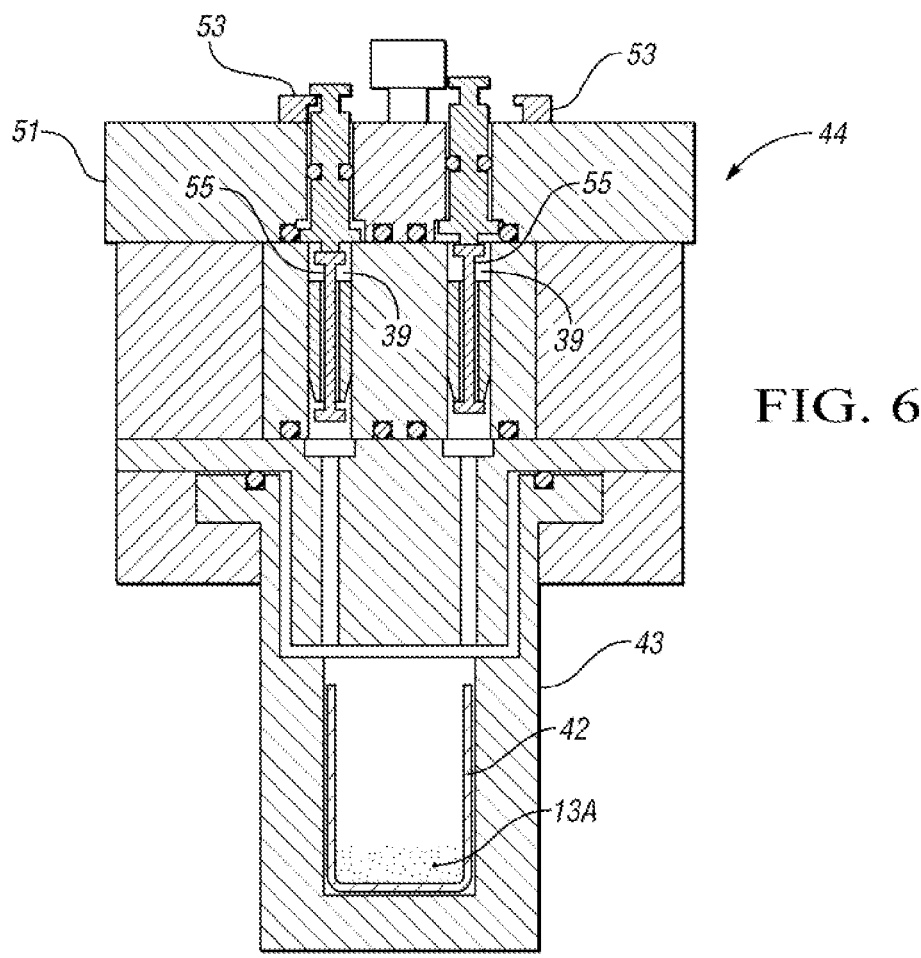
FIG. 6 is a schematic cross-sectional illustration of one embodiment of a material container assembly for holding multiple material samples taken at lines 6-6 in FIG. 7.

Each bank 17A, 17B, 17C is operatively connected to multiple sample vessels 42 with test material 13A-13F loaded into the vessels 42. Each vessel 42 may be a glass vial placed in a test well 43, shown in FIG. 6, of the material container assembly 44. In FIG. 6, only one test well 43 and one vessel 42 are shown. However, the material container assembly 44 could be extended to support multiple wells. After the vessels 42 are placed in the test well 43, the material container assembly 44 is then sealed and readied for use. Seals are generally O-rings or metal seals and the material container assembly 44 is normally held closed with fasteners.

The material container assembly 44 contains a valve 55, such as a Schrader valve, which allows the atmosphere in the test vessels 42 to be closed if it needs to be controlled. Any material container assembly 44 configured to contain test material such as 13A-13F within a controlled atmosphere may be used.

Figure 7:
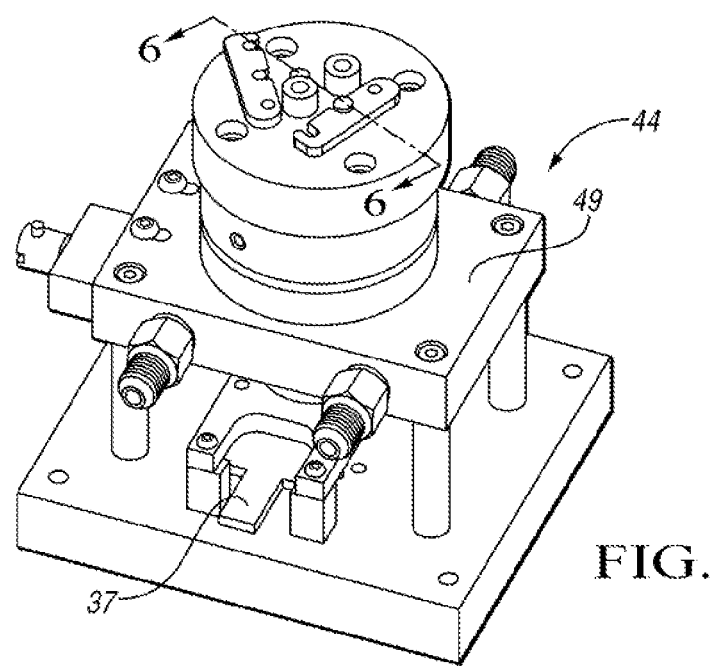
FIG. 7 is a schematic perspective illustration of the material container assembly of FIG. 6 insulated in a heated nest of a temperature control assembly.

For example, U.S. Patent Application Publication No. 20120087834A1, Apparatus For Synthesis and Assaying of Materials, filed Oct. 12, 2010, which is hereby incorporated by reference in its entirety, discloses a well assembly, lid assembly, and cap plate assembly, as well as a temperature control assembly, that may be used as a material container assembly 44 to hold material 13A as shown in FIGS. 6 and 7. The well assembly, lid assembly, and cap plate assembly, as well as a temperature control assembly are shown schematically in FIG. 6.

The material container assembly 44 is then loaded onto the device 10. It may be held in place with fasteners. The material container assembly 44 is located so that the test well 43 is surrounded by a nest 49, shown in FIG. 7, that contains heating elements 37 that are used to heat the samples of material 13A-13F in the vessels 42, when required. In one embodiment, the heating elements 37 are configured to heat the material to 201 degrees Celsius. Once loaded into the nest 49, a gas inlet 39 of the material container assembly 44 is connected to the device 10 by a gas loading plate 51 indicated in FIG. 6. The gas loading plate 51 allows fluid communication between the test materials 13A-13F and passages 46 of FIG. 1A so that the test gases can be delivered to the test materials 13A-13F in the vessels 42. The gas loading plate 51 also contains a mechanism 53 that can open and close the valve 55 on the material container assembly 44. Although two valves 55 are shown in FIG. 6, only one valve 55 is needed to provide fluid communication between the passage 46 and the test materials 13A-13F. Other material container assemblies, including a multi-well material container assembly disclosed in U.S. Pat. No. 7,767,151, High Throughput Mechanical Alloying and Screening, filed Aug. 3, 2005, which is hereby incorporated by reference in its entirety, may be used as the material container assembly supporting the vessels 42 containing materials 13A-13F.

Seals used within the device 10 may be metal, Kalrez® perfluoroelastomers, polychlorotrifluoroethylene (PCTFE), or another suitable material. Other wetted materials, such as the passages and channels, may be 316 stainless steel or another suitable material. Other suitable material options for seals, passages, and channels of the device may also be used. The gas composition measurement device 70 may be a residual gas analyzer ("RGA"). The RGA 70 may have a mass range of 100 atomic mass units, may operate with an enclosed ion source, and may be designed for 1 mTorr of inlet pressure. Many other options may also be utilized.

Referring to FIG. 1A, each channel 40 has a valve referred to as a first valve 60 ("Valve 1"). The first valve 60 may be an on/off solenoid valve, or a different valve type familiar to those knowledgeable in the art. When the material container assembly 44 is loaded onto the device 10, an initial step in preparing the device 10 to run a test is to vacuum out all of the lines from the outlet 14 of the delivery manifold 12 upstream to the material container assembly 44. This ensures that no air or other gas remains in the lines, as this could contaminate the samples of materials 13A-13F.

It may be necessary when characterizing some of the test materials 13A-13F to be able to measure gas adsorption in the presence of humidity. Due to the characteristics of water and its inherent difficulty to fully remove from device manifolds and lines, the error associated with directly measuring the concentration of water is prohibitively large because water from previous measurements results in high water backgrounds. To avoid this issue, a reference gas of a known concentration can be used to quantify the amount of other gas species that is sorbed in the test materials 13A-13F. The reference gas must be one that will not be sorbed by the test materials 13A-13F. Helium is one reference gas that can be used with many sample materials. When measuring $CO_2$ and/or $N_2$ as the sorbed gas, a helium reference gas (typically between 1-10% helium) mixed with $CO_2$ and $N_2$ and water vapor is in fluid communication with the gas input 16A. By knowing the helium concentration, the concentration of $CO_2$ and $N_2$ can be determined. This allows for calculation of adsorption and selectivity for the sample material without directly measuring the amount of water that was sorbed by the sample material. This helium reference method can be used for any mixed component gases, and is not limited to just $CO_2$ and $N_2$. Accuracy involving humid gas mixtures can be improved through methods other than a helium reference. For example, by recording the gas sample pressure in channel 40 before sampling to the RGA 70 and by knowing the steps used to reduce pressure to the RGA 70 (in the pressure reduction systems 11A-11G), the gas concentrations for each channel 40 can be accurately determined in the presence of water.

In order to create humid gas mixtures on the device 10, a water vapor dosing method is implemented. This consists of a closed cylinder filled with water in fluid communication with gas input 16E. The cylinder is temperature controlled. By varying the temperature of the liquid water, the vapor pressure in the space above the liquid is varied. This vapor pressure in the cylinder above the liquid is dosed into the device 10 to create humid gas mixtures. The water vapor can be dosed through the pressure delivery manifold 12 to fill each channel 40 with a water vapor pressure less than or equal to the water vapor pressure in the water cylinder. After dosing water into the device 10, dry gas mixtures can then be dosed through any of gas inputs 16A, 16B, 16C, 16D, resulting in a humid gas mixture of a desired concentration.

After vacuum or a desired level of humidity is established, the valves 55 of FIG. 6 operatively connected to the material container assembly 44 are then actuated by mechanisms 53 to open the vessels 42 to the outlet passage 46 of FIG. 1A. Thereafter, the first valves 60 are used to close the test samples 42 off from the rest of the device 10, and the valves 55 are left open.

Each channel 40 has another valve, referred to as the second valve 62 ("Valve 2"), which may be an on/off solenoid valve or a different valve type familiar to those knowledgeable in the art. The volume of the channel 40 between the first valve 60 and the second valve 62 is called the secondary volume and is used as a control/dosing volume for sorption measurements. Although the passages, such as channels 40, are shown schematically with a line in FIG. 1A, each passage and channel has a definitive volume.

Each channel 40 has two pressure transducers 64A, 64B located between the first valve 60 and the second valve 62. In other embodiments, only one pressure transducer is used in each channel 40. The pressure transducers 64A, 64B are referred to as pressure measurement devices and are used to monitor changes in pressure during material sorption tests. One transducer 64A is optimized for high levels of vacuum (low range pressure sensor) and the other transducer 64B is optimized for higher pressures (high range pressure sensor). In some embodiments, it may only be necessary to use a single pressure transducer for each channel 40. Based on desired accuracy, transducers may be available where a single transducer can read all desired pressures. Alternatively, if multiple transducers are needed for each channel, one or more of the transducers could be protected behind a valve. If the system pressure to be delivered will always be higher than the proof pressure of the low range transducer 64A, then monitoring of the pressure of the channel 40 can be protected by a single on/off solenoid valve, or a different valve type familiar to those knowledgeable in the art, rather than by two pressure transducers.

Separate rotary valves 66A, 66B, 66C are operatively connected to each bank 17A, 17B, 17C. The rotary valves 66A-66C each have a movable rotor 71 (indicated on rotary valve 66A) and multiple inlets. The rotor 71 is movable to connect one inlet at a time to the single outlet of the rotary valve. A separate passage 74 extends from an outlet of each of the rotary valves 66A, 66B, 66C to a respective different input of the rotary feed valve 78. Each rotary valve 66A, 66B, 66C has a single outlet that is in fluid communication with the passage 74. The rotary valves 66A, 66B, 66C and another rotary valve 78 are used to join all sample channels 40 to one output passage 68 which feeds the RGA 70. The output passage 68 shown in FIG. 1A continues in FIG. 1B, which shows the remainder of device 10. For each bank 17A, 17B, 17C, a sampling line 72 from each secondary volume (i.e., from the passage 40 between the first valve 60 and the second valve 62) is run into a separate inlet of the rotary valve 66A, 66B, or 66C creating a passage therebetween. The rotary feed valve 78 has a rotor that is used to sequentially connect each passage 74 separately and individually to the output passage 68.

Each bank 17A, 17B, 17C has a calibrated dose volume 76, represented schematically in phantom extending from the passage 74 to indicate the dose volume of the sample gas traveling through the passage 74. The dose volume 76 is the volume of sample gas that will be removed from the passage 40 by control of the valves as described herein, and sent to the RGA 70 for analysis. The dose volume 76 is minimized to ensure that removing the dose volume 76 from the passage 40 does not affect an ongoing sorption measurement. In one embodiment, the dose volume 76 is less than one percent of the system volume (i.e., less than one percent of the volume in all of the passages, channels and other conduits from the second valve 62 to the sample material (any one of 13A-13F) with the first valve 60 open).

In order to use one RGA 70, for all of the channels 40, the sample vessels 42 are brought together through the passage 46 and sampling line 72 to the rotary valves 66A, 66B, 66C. Each dose volume 76 collected in a respective passage 74 is fed into a respective inlet of the rotary feed valve 78. The channels 40, passages 46, lines 72 and passages 74 are referred to herein as a series of conduits. Alternatively, rather than multiple RGA dose volumes 76, the common ports of rotary valves 66A and 66B are tied together before going to an inlet of the rotary feed valve 78 so that there is only one RGA dose volume 76.

Figure 8:
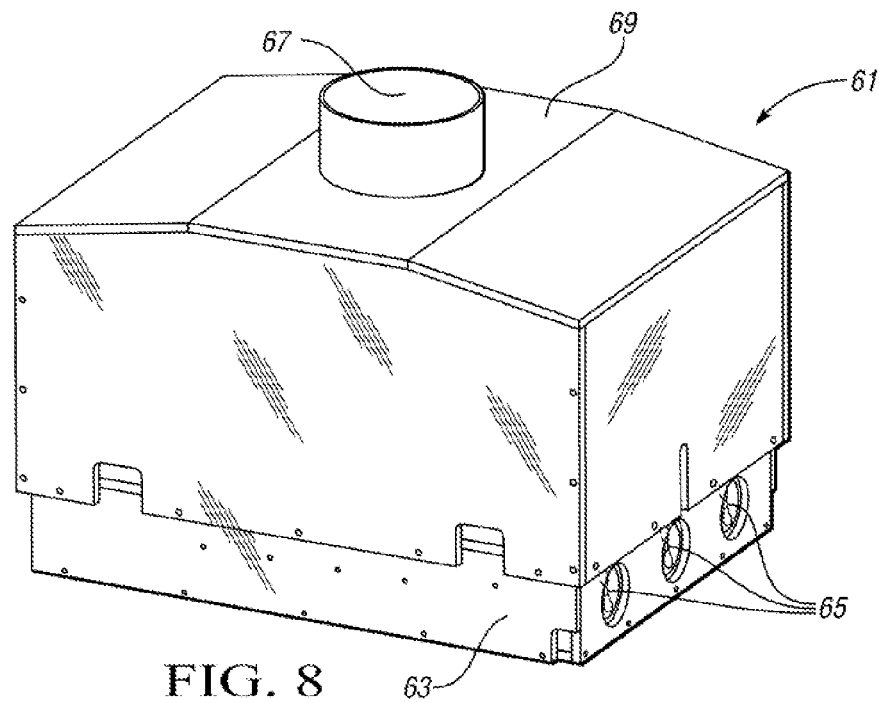
FIG. 8 is a schematic perspective illustration of a temperature controlled enclosure assembly containing a portion of the gas delivery and control system of FIG. 1A.
Figure 9:
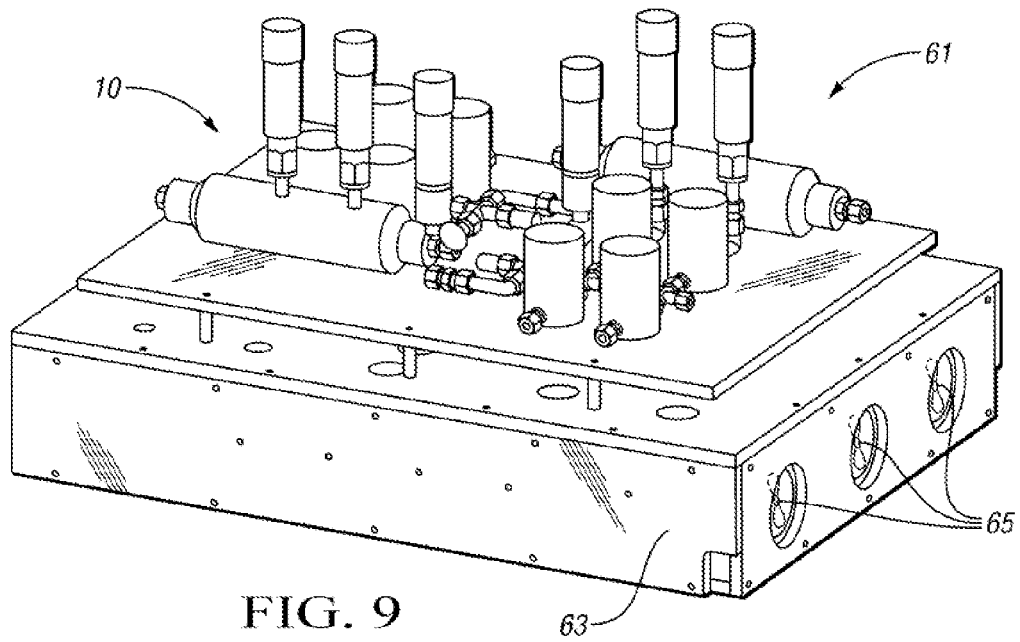
FIG. 9 is a schematic perspective illustration of a portion of the temperature controlled enclosure assembly of FIG. 8 supporting a portion of the gas delivery and control system of FIG. 1A.

In order to improve consistency of data measurements, all components of the device 10 from the outlet 14 of the delivery manifold 12 up to but not including passages 46 may be housed in a heated enclosure. By way of non-limiting example, the heated enclosure may be a temperature-controlled enclosure assembly 61 shown in FIGS. 8 and 9. The temperature-controlled enclosure assembly 61 is also shown and described in U.S. Patent Application Publication No. 20120087834A1, Apparatus For Synthesis and Assaying of Materials, filed Oct. 12, 2010. The portion of the device 10 from outlet 14 up to but not including the passages 46 is represented in FIG. 9 and shown mounted to a base 63. Fans 65 draw air into the enclosure 61, after which the air is heated by heating elements within the base 63 to keep the components of the device 10 within the enclosure 61 at a desired temperature. A vent 67 in a cover 69 of the assembly 61 allows for an exhaust circuit to continually draw air out of the assembly 61. The inner walls of the cover 69 may be insulated to improve temperature stability. Furthermore, one controller 19 (shown in FIG. 1A) may be operable to control the device 10, the temperature of heaters in the temperature-controlled enclosure assembly 61, as well as the RGA 70.

Referring to FIG. 1B, the RGA 70 is a commercially available device that measures the masses of components in a gas, thereby allowing a determination of the gas composition. The RGA 70 can only accept a limited pressure range at its inlet. Since the device 10 described here can operate under a large range of pressures, the pressure at the RGA feed valve 78 may be above an acceptable pressure for the RGA 70. A pressure reduction system 11A is shown in FIG. 1B that is a portion of the device 10 that reduces pressure of gas entering the RGA 70 to a level at which the RGA 70 is designed to operate. The pressure reduction system thus ensures that the pressure of gas delivered to the RGA 70 is not greater than a maximum pressure level operating parameter of the RGA 70. Multiple alternative embodiments of pressure reduction systems 11B, 11C, 11D, 11E, 11F, and 11G are shown in FIGS. 1B-1H, and may be used in place of pressure reduction system 11A in the device 10.

The pressure reduction system 11A of FIG. 1B includes a pressure vessel 80 defining an expansion volume 82. The RGA feed valve 78 of FIG. 1A connects to the expansion volume 82 via the output passage 68. The expansion volume 82 is selectively connected to a turbopump 84 when a solenoid valve 86 is in an open position. The turbopump 84 is used before introducing gas to the expansion volume 82 to bring the expansion volume 82 to a high level of vacuum, ensuring that the pressure in the expansion volume 82 is as close to zero as possible. The expansion volume 82 is designed to ensure that the sample pressure delivered in the output passage 68 is expanded to a pressure that will be within the operating parameters of the RGA 70. If the pressure after expansion is too high, a passage 87 connected to a vacuum source can be opened by a valve 88 that can be a pneumatic valve or a solenoid valve. An orifice 89 formed in the passage 87 allows the expansion volume 82 pressure to bleed down slowly. A pressure transducer 90 is used to measure the pressure of the gas in the expansion volume 82. Once the pressure is acceptable for the RGA 70, the valve 88 closes. Another solenoid valve 92 to the RGA 70 is then opened, allowing flow from the expansion volume 82 to the RGA 70 through a passage 94 so that the gas sample can be measured by the RGA 70.

An alternative embodiment of a pressure reduction system 11B that may be used as part of the device 10 in place of the pressure reduction system 11A in FIG. 1B is shown in FIG. 1C. To avoid fractionation, the pressure reduction system 11B has a rotary expansion volume selector valve 78A to connect the sample output passage 68 to multiple expansion volumes 82A, 82B, 82C defined by pressure vessels 80A, 80B, and 80C. The valve 78A is left open in communication between the passage 68 and the selected expansion volume 82A, 82B, 82C until pressure equalizes. The extended opening of the valve 78A and the absence of narrow apertures or other restrictions prevents fractionation of a mixed gas. Many of the pressure reduction systems 11C-11G described below also have multiple expansion volumes and large apertures that help to avoid fractionation of mixed gas. Pressure transducers 90A, 90B, 90C are used to measure the pressure of the gas in the respective expansion volumes 82A, 82B, 82C. No vacuum pressure reduction is used in the pressure reduction system 11B, as the expansion volumes 82A, 82B, 82C are designed to reduce the entire range of system pressures to pressures within the operating parameters of the RGA 70. The expansion volumes 82A, 82B, 82C are selectively connected to the turbopump 84 when a respective solenoid valve 86A, 86B, 86C is in an open position. The turbopump 84 is used before introducing gas to the expansion volume 82A, 82B, 82C to bring the expansion volume 82A, 82B, 82C to a high level of vacuum, ensuring that the pressure in the expansion volume 82A, 82B, 82C is as close to zero as possible. A separate passage 91A, 91B, and 91C extends from each of the pressure vessels 80A, 80B, 80C to connect the expansion volumes 82A, 82B, 82C to a second rotary RGA feed valve 92A ("RGA Feed Valve 2") that connects the multiple expansion volumes 82A, 82B, 82C to the single RGA 70. Additional expansion volumes may also be included in the pressure reduction system 11B.

Another alternative embodiment of a pressure reduction system 11C that may be used as part of the device 10 in place of the pressure reduction system 11A in FIG. 1B is shown in FIG. 1D. The pressure reduction system 11C has three pressure vessels 80A, 80B, 80C defining three expansion volumes 82A, 82B, 82C. The expansion volumes 82A, 82C are in selective fluid communication with the expansion volume 82B by selective on/off solenoid valves 86D, 86E. The expansion volume 82B is referred to as the main expansion volume. The outlet passage 68 is in selective fluid communication with the expansion volume 82B by a selective on/off solenoid inlet valve 85. Before feeding the expansion volume 82B, the pressure transducers 64A, 64B of FIG. 1A and the controller 19 determine test gas pressure, and determine which combination of expansion volumes 82A, 82B, 82C will reduce the test gas pressure to a range within the operating parameters of the RGA 70. That is, a determination is made as to whether either of both of the expansion volumes 82A and 82C should be added to the expansion volume 82B to obtain a desirable test gas pressure. The valve 86D and/or 86E is then opened to place the expansion volume 82A and/or 82C in fluid communication with expansion volume 82B if it is determined that the expansion volumes 82A and/or 82C are needed. Solenoid valve 86 is opened and the turbopump 84 pulls expansion volume 82B and any of the expansion volumes 82A and/or 82C to ultrahigh vacuum. Valve 86 is then closed and an on/off solenoid inlet valve 85 is opened to allow the sample gas to enter the expansion volume 82B and any of expansion volumes 82A and 82C in fluid communication therewith. The inlet valve 85 is then closed. After expansion, solenoid valve 92 is opened to allow the test gas to enter the RGA 70 for testing. The multiple expansion volumes 82A, 82B, 82C help to avoid fractionation of mixed gas. Additional expansion volumes may also be included in the pressure reduction system 11C.

Figures 1E, 1F:
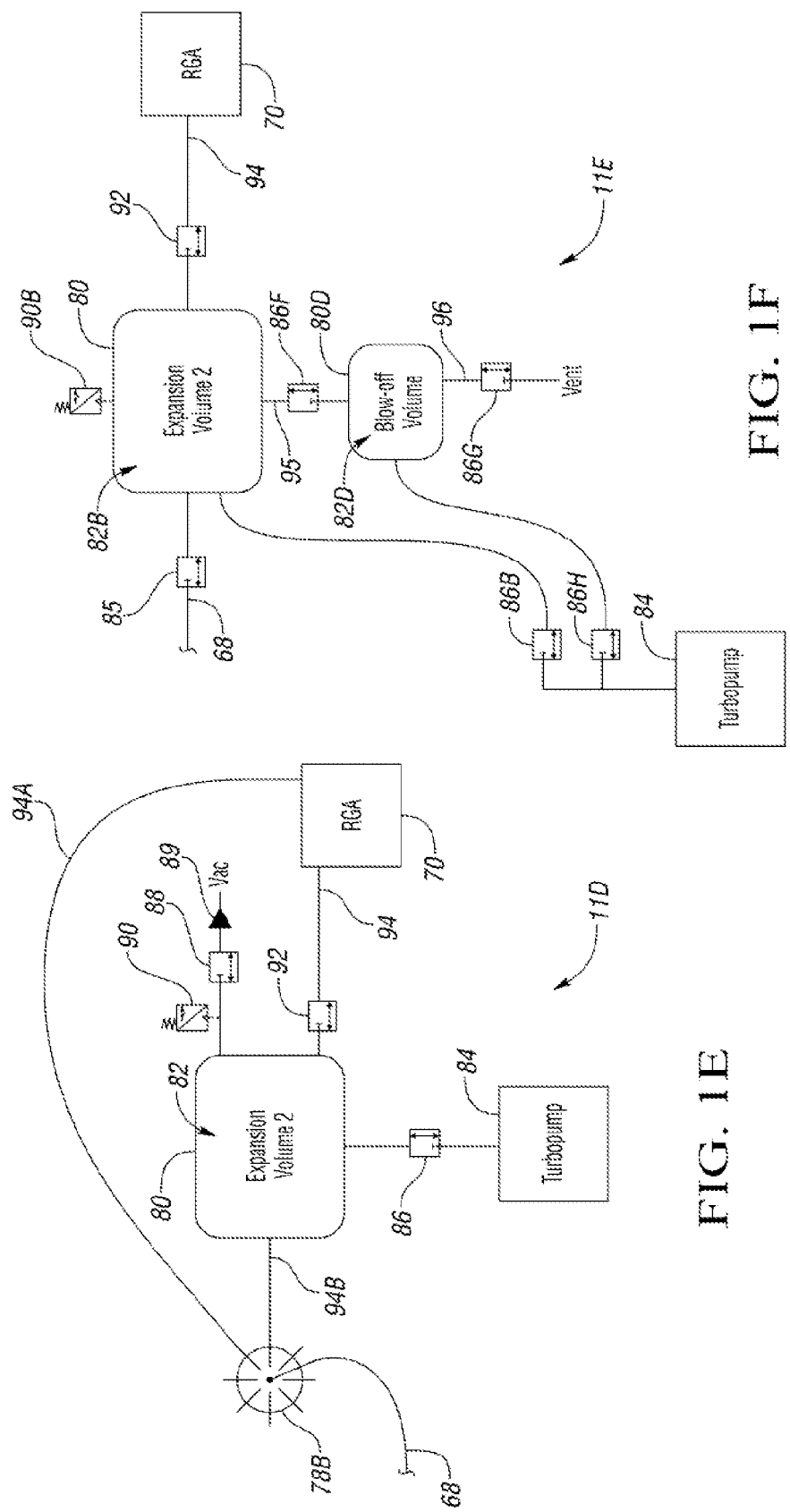
FIG. 1E is a schematic illustration of an alternate remainder of the device of FIG. 1A showing a fourth embodiment of a pressure reduction system.
FIG. 1F is a schematic illustration of an alternate remainder of the device of FIG. 1A showing a fifth embodiment of a pressure reduction system.

Another alternative embodiment of a pressure reduction system 11D that may be used as part of the device 10 in place of the pressure reduction system 11A in FIG. 1B is shown in FIG. 1E. The pressure reduction system 11D provides two separate passages, first passage 94A and second passage 94B, that may be used to feed the test gas to the RGA 70. The first passage 94A is referred to as a bypass passage as it bypasses the remainder of the pressure reduction system 11D. A rotary selector valve 78B selects the passage 94A, 94B that is to be used depending on the test gas pressure delivered in passage 68 as indicated by pressure transducers 64A, 64B of FIG. 1A. Passage 94B feeds into the expansion volume 82. If the pressure is below a predetermined level, the selector valve 78B is controlled so that the gas follows a relatively low pressure path along passage 94A directly to the RGA 70. A direct feed to the RGA 70 avoids the step of expanding the test gas in the expansion volume 82, thus reducing overall test time. If the pressure in passage 68 is above the predetermined level, the selector valve 78B is controlled so that the gas is fed into expansion volume 82 through passage 94B, and then is selectively fed into the RGA 70 through passage 94 when RGA feed valve 92 is open. The turbopump 84, solenoid valve 86, pressure transducer 90, solenoid valve 88 and orifice 89 function as described with respect to FIG. 1B. The expansion volume 82 helps to avoid fractionation of mixed gas. Additional expansion volumes may also be included in the pressure reduction system 11D.

Another alternative embodiment of a pressure reduction system 11E that may be used as part of the device 10 in place of the pressure reduction system 11A in FIG. 1B is shown in FIG. 1F. As in the embodiment of FIG. 1D, the turbopump 84 is selectively in communication with the expansion volume 82B by the opening of solenoid valve 86B to pull the expansion volume 82B to a vacuum before opening the on/off solenoid inlet valve 85 to allow test gas to enter the expansion volume 82B. In the pressure reduction system 11E, an additional pressure vessel 80D defines an additional volume referred to as a blow-off volume 82D. The expansion volume 82B is in selective fluid communication with the blow-off volume 82D through a connecting passage 95 when an on/off solenoid valve 86F is opened. If the pressure in the expansion volume 82B is above a predetermined pressure, the on/off solenoid valve 86F is opened so that the expansion volume 82B vents to the blow-off volume 82D, allowing the pressure in the expansion volume 82B to fall. The on/off valve 86F is then closed and a selectively openable on/off solenoid valve, referred to as a vent valve 86G, is opened to empty the blow-off volume 82D through a vent passage 96. If the pressure in the expansion volume 82B is still above the predetermined pressure, a selectively openable on/off solenoid valve 86H is opened so that the blow-off volume 82D may be vacuumed down by the turbopump 84. Valve 86H is then closed and the solenoid valve 86F is then reopened to vent additional test gas from the expansion volume 82B to the blow-off volume 82D, thus reducing the pressure in the expansion volume 82B. The vent valve 86G is then opened to vent the blow-off volume 82D. The process of venting test gas to the blow-off volume 82D, venting the blow-off volume 82D, and using the turbopump 84 as necessary, is repeated until an acceptable pressure below the predetermined pressure is reached in the expansion volume 82B for feeding to the RGA 70. The expansion volume 82B helps to avoid fractionation of mixed gas. Additional expansion volumes may also be included in the pressure reduction system 11E.

Figures 1G, 1H:
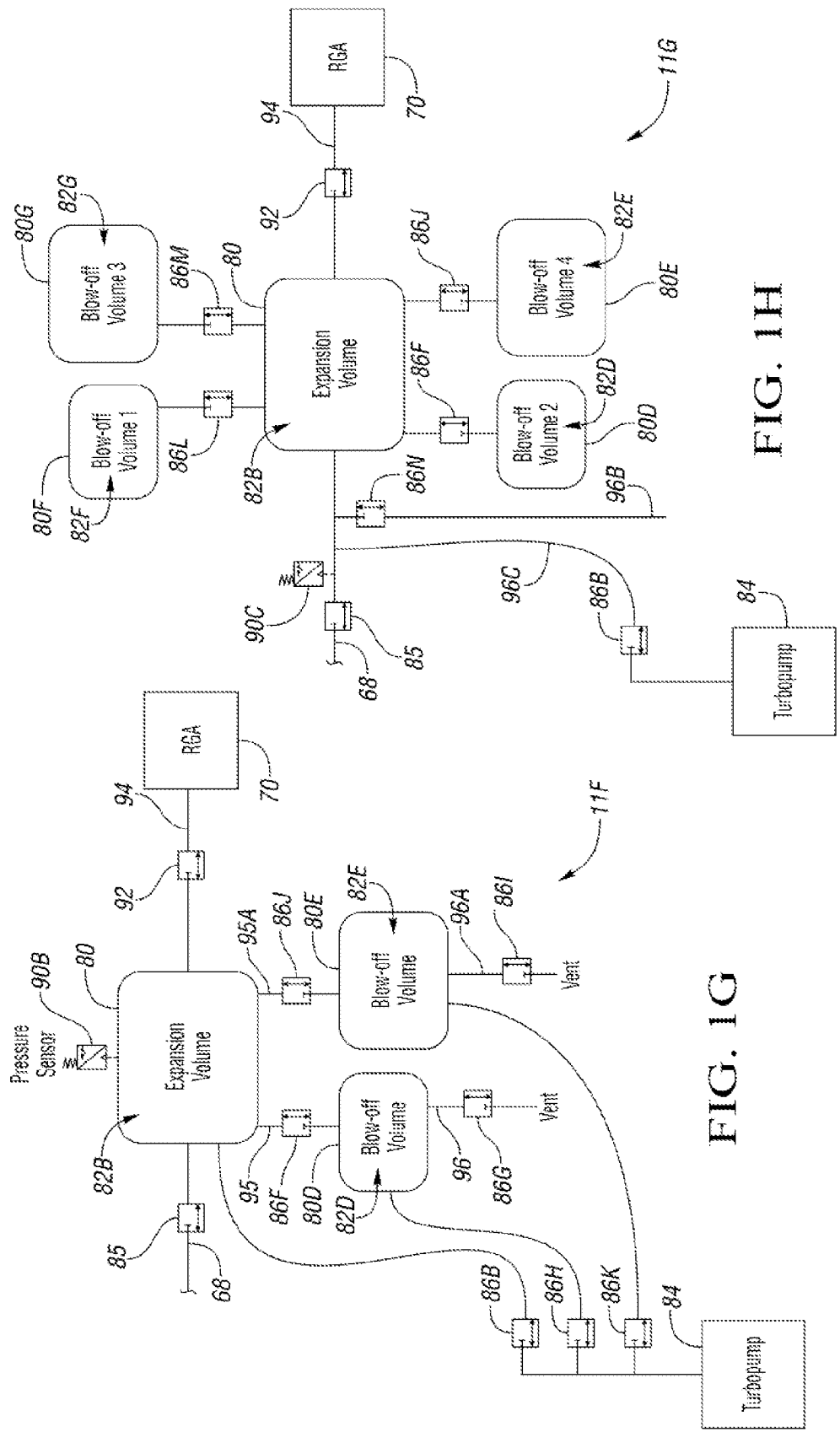
FIG. 1G is a schematic illustration of an alternate remainder of the device of FIG. 1A showing a sixth embodiment of a pressure reduction system.
FIG. 1H is a schematic illustration of an alternate remainder of the device of FIG. 1A showing a seventh embodiment of a pressure reduction system.

Another alternative embodiment of a pressure reduction system 11F that may be used as part of the device 10 in place of the pressure reduction system 11A in FIG. 1B is shown in FIG. 1G. The pressure reduction system 11F is similar to the pressure reduction system 11E of FIG. 1F, except that at least one additional blow-off volume 82E formed by a different pressure vessel 80E is also in selective fluid communication with the expansion volume 82B by a separate passage 95A openable via a selective on/off solenoid valve 86J, allowing flexibility to blow off a larger amount of gas from the expansion volume 82B at a given time (i.e., blow-off gas may be sent to both blow-off volumes 82D and 82E at the same time), thereby reducing the time to get to an acceptable pressure in the expansion volume 82B for feeding to the RGA 70. For example, if both blow-off volumes 82D and 82E are used, the pressure level in the expansion volume 82B may be low enough to allow opening of the RGA feed valve 92 without using the turbopump 84 to repeatedly vacuum the blow-off volumes 82D, 82E. The additional blow-off volume 82E is also in selective communication with the turbopump 84 by a selectively openable on/off solenoid valve 86K. Both of the blow-off volumes 82D and 82E may be vacuumed at the same time by opening solenoid valve 86H as well as the additional solenoid valve 86K. The blow-off volumes 82D, 82E are separately vented through vent lines 96 and 96A by control of solenoid valves 86G, 861, respectively. The expansion volume 82B helps to avoid fractionation of mixed gas. Additional expansion volumes may also be included in the pressure reduction system 11F.

Another alternative embodiment of a pressure reduction system 11G that may be used as part of the device 10 in place of the pressure reduction system 11A in FIG. 1B is shown in FIG. 1H. The pressure reduction system 11G has multiple blow-off volumes 82D, 82E, 82F, and 82G formed by multiple respective pressure vessels 80D, 80E, 80F and 80G in selective fluid communication with the expansion volume 82B in pressure vessel 80 by respective controllable on/off solenoid valves 86F, 86J, 86L, and 86M. The controller 19 of FIG. 1A opens one of more of the solenoid valves 86F, 86J, 86L, and 86M as needed to achieve a desired pressure within the expansion volume 82B, as may be indicated by the pressure transducer 90C. Any open ones of the solenoid valves 86F, 86J, 86L, and 86M are then shut, and the RGA feed valve 92 is opened to provide the test gas from the expansion volume 82B to the RGA 70. If needed, test gas can be stored in some or all of the expansion volumes 82D, 82E, 82F, 82G while volume 82B and the volumes 82D, 82E, 82F, 82G not used for storage are evacuated. This may be done if initial expansion into all volumes does not reduce the pressure low enough for sampling to the RGA 70. This significantly reduces the number of steps required for pressure reduction. The expansion volume 82B helps to avoid fractionation of mixed gas. Additional expansion volumes may also be included in the pressure reduction system 11G.

A line 96B is placed in fluid communication with the expansion volume 82B when a solenoid valve 86N is opened. Line 96B is used for supplying mixed gases of known concentrations to the RGA 70 for calibrating the RGA 70. The turbopump 84 is applied to the expansion volume 82B and selectively to one or more of the blow-off volumes 82D, 82E, 82F and 82G through one passage 96C when the solenoid valve 86B and the respective solenoid valves 86F, 86J, 86L, and 86M are opened.

Optionally, it may be desirable to use a combination of vacuum and heat to bake out the device 10 to ensure that no residual gases remain that can contaminate a future test. For example, test gases with polar molecules such as $H_2O$ may necessitate heating. If this is the case, the entire device 10 from the RGA feed valve 78 of FIG. 1A to the RGA 70 can be enclosed in a heated enclosure or wrapped with heat tape to allow bake out.

Figure 10:
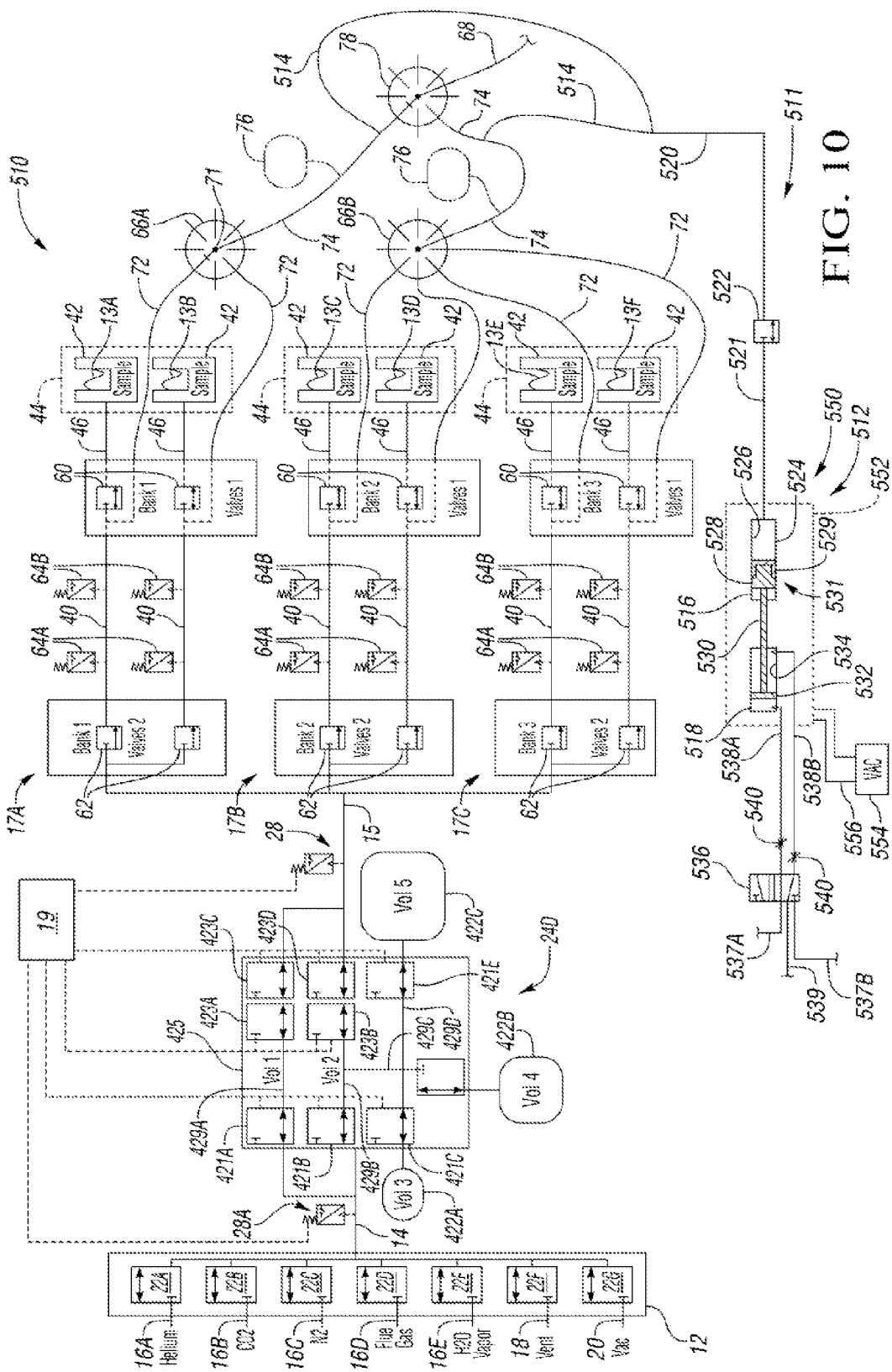
FIG. 10 is a schematic illustration of a portion of a second embodiment of a multi-channel gas sorption device including the fifth embodiment of a pressure control system and a first embodiment of a gas mixing device.

FIG. 10 shows an alternative embodiment of an apparatus referred to herein as a multi-channel gas sorption device 510. The gas sorption device 510 is similar to the multi-channel gas sorption device 10 of FIG. 1 with the pressure control system 24D of FIG. 5, and adds a mixing system 511 with a mixing device 512 to ensure that the dose volume 76 delivered to the RGA 70 has a gas composition that accurately reflects gas sorption by the material sample being tested, that is, a sample of any one of the test materials 13A-13F in the sample vessels 42. Like the gas sorption device 10 of FIG. 1, the device 510 has an output passage 68 which feeds to the RGA 70. The output passage 68 can feed to the RGA 70 through any of the pressure reduction systems 11A-11G as shown in FIGS. 1B-1H. The gas sorption device 510 has fewer rotary valves 66A, 66B than gas sorption device 10, as more lines 72 from more of the secondary volumes with channels 40 are routed to rotary valve 66B. In any of the embodiments of the gas sorption devices 10, 510, the rotary valves 66A, 66B, 66C shown herein may be connected to fewer or more lines 72 than are specifically shown, up to the maximum number of inlets on the rotor 71.

When the gas sorption device 10 or 510 described above is used to measure mixed gases, first valves 60 are closed and a chosen gas mixture is fed into the secondary volumes of channels 40 at a specified pressure. The secondary volume for each sample vessel 42 is the volume contained in channel 40 between first valves 60 and second valves 62 at a specified pressure. Second valves 62 are then closed so a fixed amount of gas is contained in the secondary volume. First valves 60 are then opened to expose the multiple test materials 13A-13F to the test gas. When one of the test materials 13A-13F absorbs a gas, the pressure in the corresponding secondary volume falls and is measured by the secondary volume transducers 64A, 64B. The pressures are observed for a given period of time and the change in pressure is used to quantify gas uptake or release from the test materials 13A-13F at various temperatures. If the gas is a mixed (multi-component) gas, the pressure change does not provide information as to which gas or gases are being sorbed. However, by taking a sample of the mixed gas after sorption and measuring it in the RGA 70, the exact gas makeup can be determined. This can be compared to the original gas composition to determine which gas was sorbed by the sample material.

In the embodiment of FIG. 10, a sampling line 72 is connected from each secondary volume 40 to a multi-position rotary valve 66A or 66B. The use of rotary valves allows many gas sample channels to be connected to one RGA 70. The RGA 70 is an expensive device and it is preferable to use only one to minimize system costs. The rotary valves 66A, 66B connect one channel 40 and sampling line 72 at a time to the RGA feed valve 78 through a fixed volume passage 74. As discussed above, in an alternative embodiment, the common ports of rotary valves 66A and 66B are tied together before going to an inlet of the rotary feed valve 78 so that there is only one RGA dose volume 76. The dose volume 76 is the internal volume of the passage 74 and the adjacent valves 66A or 66B and 78 when in the closed position. The dose volume 76 is the amount of test gas that is pulled from a channel 40 and sent to the RGA 70 for analysis, and is ideally minimized. The passages 74 are connected to the RGA 70 one at a time through the RGA feed valve 78. The channels 40, lines 72, and passages 74 are referred to herein as a series of conduits.

In order to optimize the gas sorption device 510 for accurate, high throughput gas sorption measurements while using a minimal amount of sample material, all component and line volumes through which the gas flows have been minimized. Because of this, diffusion between the primary volumes of passages 46 and the secondary volumes of channels 40 is very slow. If the device 510 relied on diffusion, this would lead the gas composition in the secondary volume to be different than the gas composition in the primary volume (where the sorption is occurring) after the test material 13A, 13B, 13C, 13D, 13E or 13F has been exposed to the test gas. As the sample material absorbs one component of a mixed gas, the concentration of that gas falls in the primary volume. The time to achieve equilibrium between the primary volume and the secondary volume using only diffusion can be exceedingly slow. For example, with a passage 46 that is 0.125 inches in diameter and 12 feet long, it would take 145 hours for the gases in the primary and secondary volumes to come to equilibrium, which is unacceptable for commercial testing purposes. Until equilibrium is achieved, however, the gas that is sampled from the secondary volume for RGA testing will not give an accurate measurement of gas composition and the sorption characteristics of the materials 13A-13F thus cannot be determined.

In order to ensure that the gas composition is the same in each paired primary volume (i.e., the volume within passage 46) and secondary volume (i.e., the volume within channel 40), the mixing system 511 with the mixing device 512 for forced gas mixing of the primary volume, secondary volume and dose volume is provided. A respective line 514 operable to permit gas flow is connected to each dose volume 76. The lines 514 connect together into one line 520 that is in fluid communication with the mixing device 512 through another line 521 when a mixing pump selection valve 522 is in an open position.

The mixing device 512 includes a mixing pump 516 and an actuator 518 that cycles the mixing pump 516 as described herein. The actuator 518 can be connected to a controller (such as controller 19 of FIG. 1A) that can automatically energize the actuator 518 to cycle the pump 516 according to a predetermined cycling period correlated with a test gas that sufficiently mixes the gas in the conduits so that the gas composition in the secondary volume is substantially identical to the gas composition within the primary volume. Alternatively, the actuator 518 can be energized by a user manually closing a switch. As used herein, gas compositions of two volumes of gasses are "substantially identical" if the distribution of the component gasses are within the accuracy of the instrument used to measure gas composition. For example, in one embodiment, gas compositions of two volumes are "substantially identical" if they are at least 99 percent identical. In another embodiment, gas compositions of two volumes are "substantially identical" if they are at least 99.9 percent identical. In still another embodiment, gas compositions of two volumes are "substantially identical" if they are at least 99.99 percent identical.

The mixing pump selection valve 522 is included to operatively disconnect the mixing pump 516 from the multi-channel gas sorption device 510 when requested by the user. That is, the mixing pump selection valve 522 is closed, and the mixing pump 516 is therefore not in fluid communication with the line 520 and the rotary feed valve 78. The mixing pump selection valve 522 may not be necessary in all embodiments. The mixing pump 516 has a pump body 524 that has a bore 526 in which a plunger 528 moves cyclically back and forth. The plunger 528 can have a plunger seal 529 that is interference fit to the pump body 524 in the pump bore 526. Together, the plunger 528 and plunger seal 529 are referred to as a plunger assembly 531.

In the gas sorption device 510 of FIG. 10, the actuator 518 is an air cylinder that is connected via a connecting rod 530 to the plunger 528 to cause the plunger 528 to reciprocate in the bore 526. One end of the bore 526 is open to the line 521. The air cylinder 518 moves the plunger 528 between open and closed positions. The air cylinder motion is translated to the plunger 528 by the connecting rod 530. In other embodiments the air cylinder 518 is replaced with a linear actuator or a motor/ball screw combination. The position of a land 532 of the air cylinder 518 within a bore 534 of the air cylinder 518 is controlled by an electrically actuated selector valve 536 that controls air flow from a pressurized air feed 539 to portions of the bore 534 on opposite sides of the land 532 through lines 538A, 538B. The pressurized air feed 539 is in fluid communication with the line 538B in FIG. 10 to provide pressurized air to the portion of the air cylinder 518 on the right side of the land 532, and is placed in fluid communication with the line 538A to provide pressurized air to the portion of the air cylinder 518 on the left side of the land 532 when the valve 536 is actuated to shift downward in FIG. 10. The valve 536 is electronically controlled to shift up and down as described to alternately allow pressurized air to line 538B and exhaust air through line 538A to exhaust line 537A, and exhaust air through line 538A and exhaust line 537B while allowing pressurized air to line 538A. Reciprocation of the valve 536 thereby causes cycling of the plunger 528 in the bore 526. Restrictive orifices 540 are placed in the lines 538A, 538B between the selector valve 536 and the air cylinder 518 to control the speed of the air cylinder 518. The restrictive orifices 540 slow the flow of air to the air cylinder 518.

To obtain accurate gas composition measurements using the RGA 70, the mixing system 511 is designed to prevent air from leaking into the line 520 and affecting the composition of the dose volume 76. Although the plunger seal 529 described herein is designed to minimize leakage, because it is a sliding seal, the possibility of leakage must be considered. Accordingly, the mixing system 511 is configured with a vacuum device 550 to prevent air leaks. The vacuum device 550 is configured to ensure that if a leak does occur between the seal 529 of the plunger assembly 531 and the pump body 524 at the bore 526, air will not leak in, but test gas will leak out. Although this will reduce the amount of sample gas available to the RGA 70, the gas that is supplied will be the correct composition (i.e. a composition accurately reflecting gas sorption by the test material). In the gas sorption device 510, the vacuum device 550 includes a vacuum enclosure 552 that surrounds both the air cylinder 518 and the mixing pump 516. A vacuum 554 is connected to the vacuum enclosure 552 through a connecting line 556 and is operable to place the volume within the vacuum enclosure 552 under a vacuum. All lines 521, 538A, 538B, 556 running into the enclosure 552 are sealed to the enclosure 552 to ensure that it is leak free. When the mixing device 512 is in operation, a high level of vacuum is applied to the vacuum enclosure 552. Since the pressure in the enclosure 552 is lower than the test gas pressure, and the vacuum 554 has removed the air in the enclosure 552, air cannot leak into the dose volume 76 through the lines 520 and 521 and affect the gas composition measurements.

Figure 11:
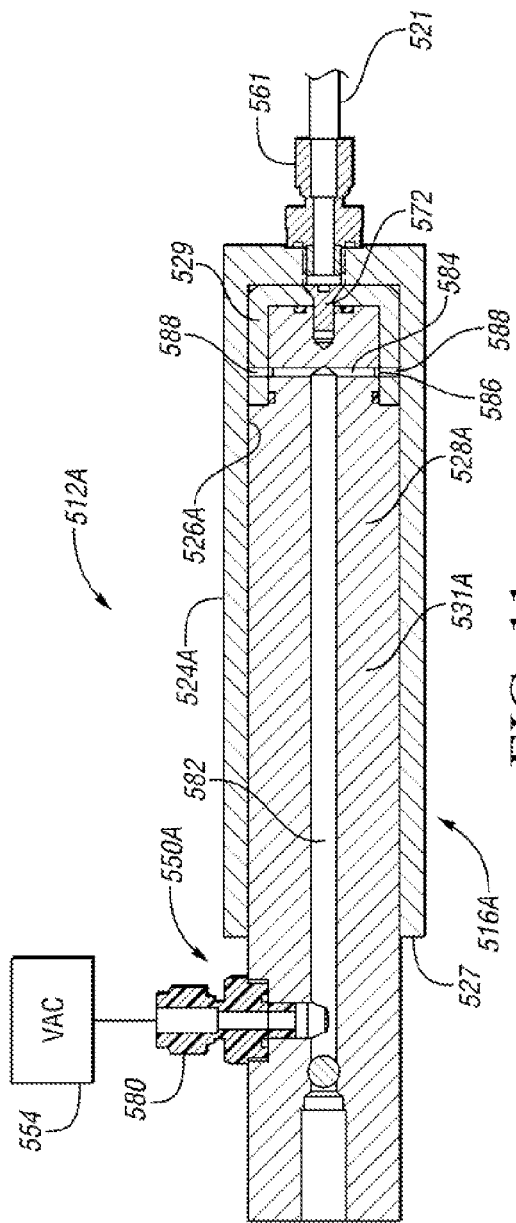
FIG. 11 is a schematic cross-sectional illustration of a second embodiment of a gas mixing device for use with the multi-channel gas sorption device of FIG. 10.

FIG. 11 shows a cross-sectional view of another embodiment of a mixing device 512A with a mixing pump 516A that can be used in place of the mixing device 512 and mixing pump 516 in the mixing system 511 of FIG. 10. The mixing pump 516A includes a pump body 524A and a plunger assembly 531A. The pump body 524A is a cylindrical barrel defining a bore 526A, open at one end 527 and connected to line 521 on the other end through a fitting 561. The plunger assembly 531A is assembled through the open end 527 and positioned in a bore 526A of the pump body 524A. The plunger assembly 531A is designed to seal against the inner surface of the pump body 524A in the bore 526A. To enable a high quality seal, the plunger assembly 531A is configured with a plunger 528A on which a plunger seal 529A is mounted. The plunger 528A is a stiff body made from aluminum, stainless steel or a stiff plastic. The plunger 528A is designed to have a tight fit to the bore 526A in order to keep the plunger assembly 531A properly aligned as it travels between the closed position of FIG. 11 and the open position of FIG. 12. The actuator 518 of FIG. 10 is operatively connected to the mixing pump 516A in the same manner as described with respect to the mixing pump 516 of FIG. 10.

Figure 12:
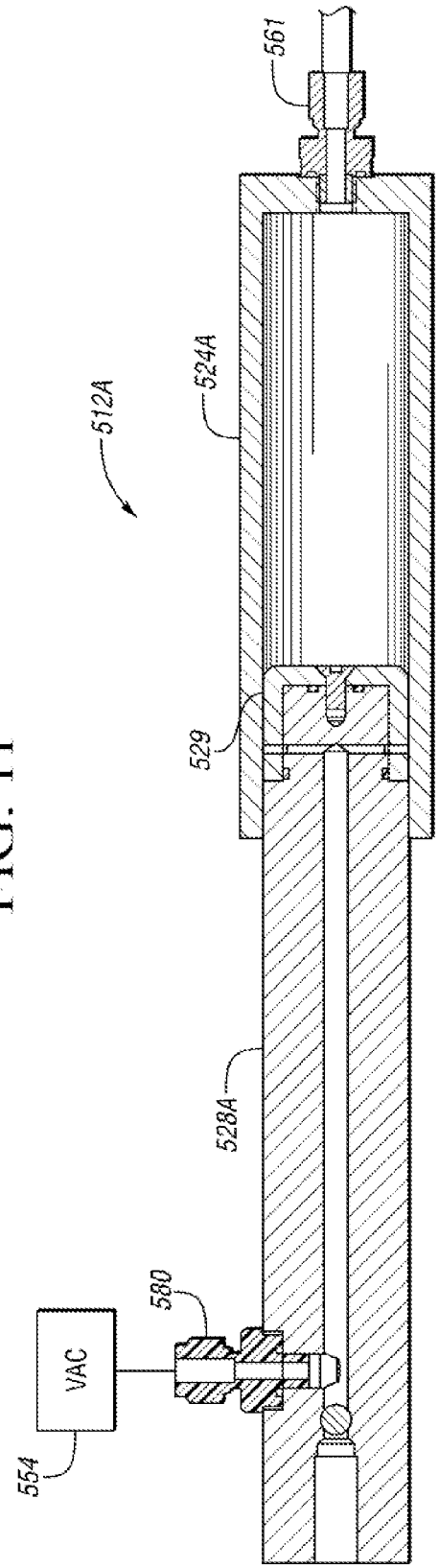
FIG. 12 is a schematic cross-sectional illustration of the gas mixing device of FIG. 11 with a pump body having a plunger assembly in a bore of the pump body and actuated to a different position.
Figure 13:
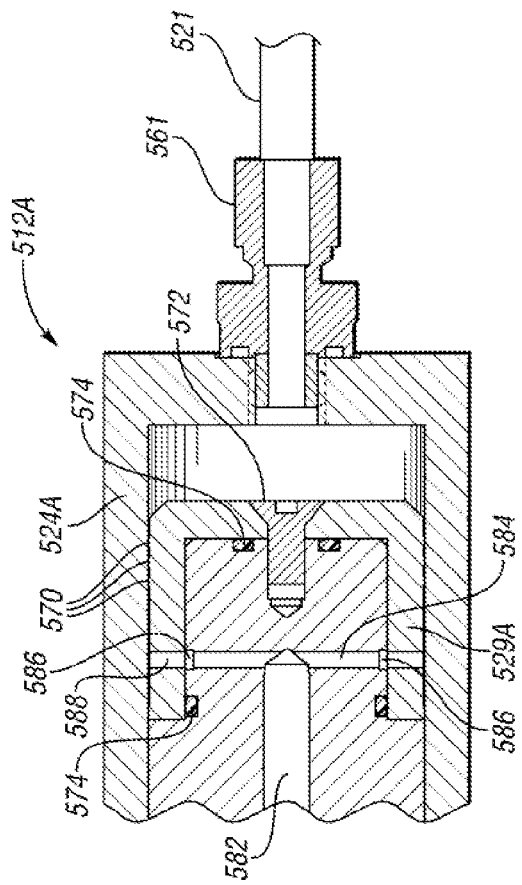
FIG. 13 is a schematic cross-sectional illustration in fragmentary view of a portion of the gas mixing device of FIGS. 11 and 12.
Figure 14:
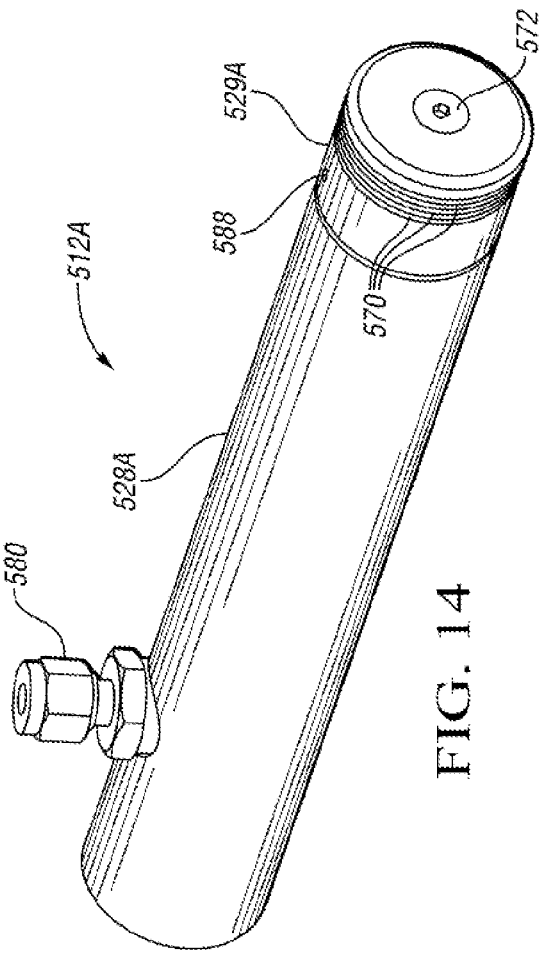
FIG. 14 is a schematic perspective illustration of the plunger assembly of FIG. 11.

The plunger seal 529A can be made out of a compliant plastic such as Teflon (PTFE). The plunger seal 529A has seal ridges 570 that are best shown in FIGS. 13 and 14. The seal ridges 570 are annular and completely surround the plunger seal 529A. The seal ridges 570 come into contact with the inner surface of the pump body 524A in the bore 526A, as best shown in FIG. 12. The interference fit between the seal ridges 570 and the pump body 524A is designed to provide maximum sealing capability while still allowing the plunger assembly 531A to slide in the bore 526A. In this embodiment, the plunger seal 529A has four seal ridges 570 to provide redundancy, but fewer or more seal ridges could be provided. The plunger seal 529A is attached to the plunger 528A by a screw 572. An additional seal between the plunger seal 529A and the plunger 528A is provided by two O-rings 574 shown in FIG. 13.

The mixing pump 516A is used with an alternate design of a vacuum device 550A shown in FIG. 11. In this embodiment, instead of surrounding the mixing pump 516A with vacuum, the vacuum is run through the center of the plunger 528A. The vacuum source 554 is connected to the plunger 528A by a fitting 580. The fitting 580 has a central opening that is in fluid communication with a passage 582 down the center of the plunger 528A. The passage 582 intersects a hole 584 that extends radially, perpendicular to the passage 582, through the plunger 528A. The hole 584 intersects a groove 586 that extends around the outer circumference of the plunger 528A. When the plunger seal 529A is assembled onto the plunger 528A, a hole 588 that is cut through the plunger seal 529A lines up with the groove 586. The hole 588 is located between the third and fourth seal ridges 570 furthest from the end of the plunger seal 529A at the screw 572, so that vacuum can be applied to the space between the third and fourth seal ridges 570 and the pump body 524A. Like the vacuum enclosure 552 of the embodiment of FIG. 10, the vacuum device 550A prevents air from entering the dosing volume 76 through the lines 520, 521 via the mixing device 512A. If the first three seal ridges 570 fail and create a gas leak, the vacuum applied between the third and fourth seal ridges 570 will cause the test gas to leak out. Although there will be less test gas, the composition of the test gas remaining in the dosage volume 76 will be unaffected, so that accurate gas composition measurements can still be made by the RGA 70.

Figure 15:
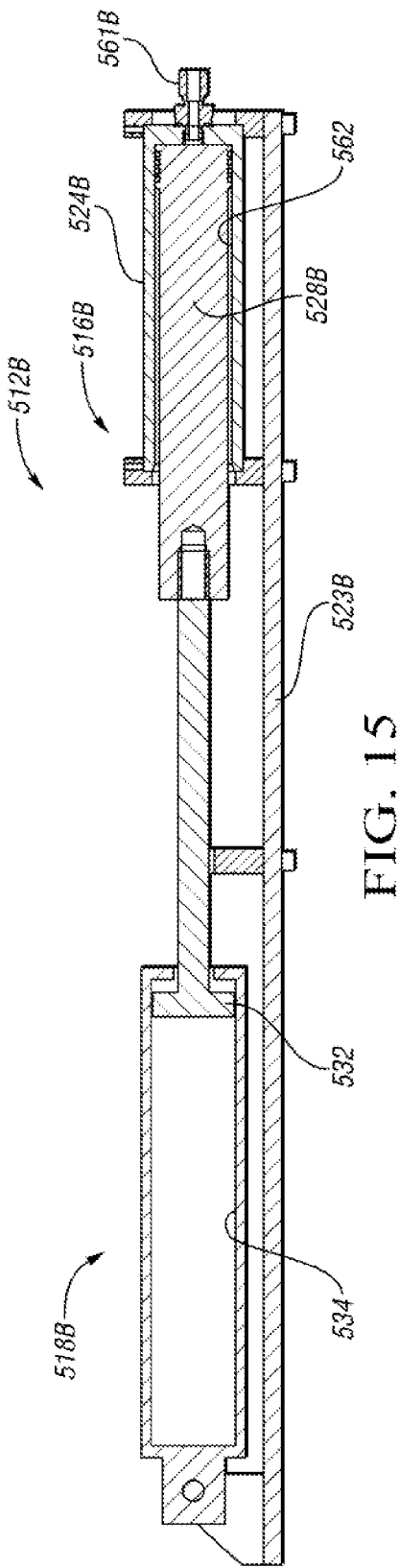
FIG. 15 is a schematic cross-sectional illustration of a third embodiment of a gas mixing device for use with the multi-channel gas sorption device of FIG. 10.

FIG. 15 shows a cross-sectional view of another embodiment of a mixing device 512B with a mixing pump 516B that can be used in place of the mixing device 512 and mixing pump 516 in the mixing system 511 of FIG. 10. Components of the mixing device 512B and mixing pump 516B that are identical in structure and function to the mixing device 512 and the mixing pump 516 are indicated with like reference numbers. The mixing pump 516B has a pump body 524B that is a cylindrical barrel defining a bore 526B, open at one end 527B and connected to line 521 of FIG. 10 on the other end through a fitting 561B.

Figure 16:
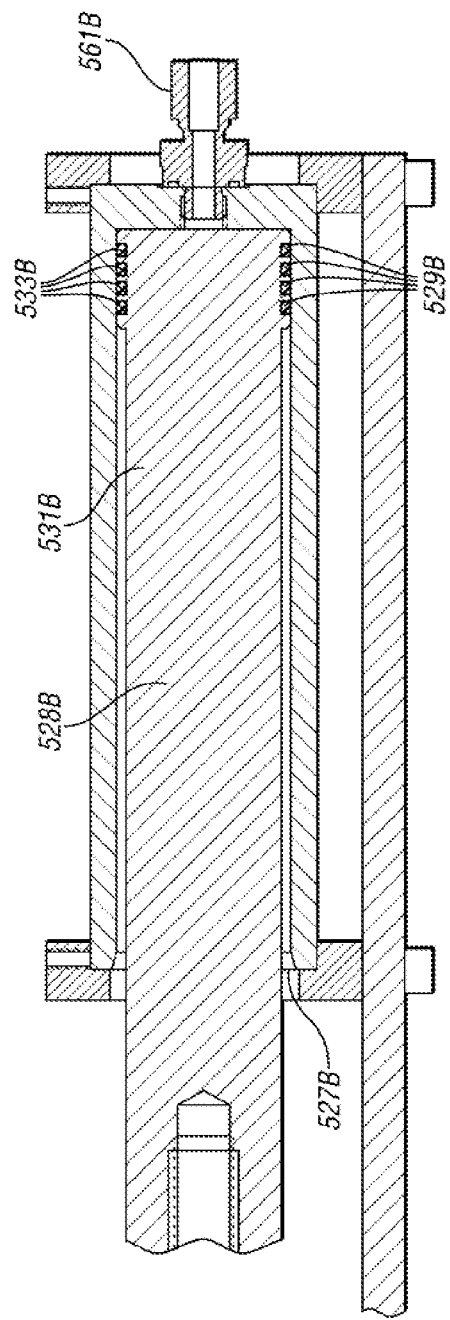
FIG. 16 is a schematic cross-sectional illustration of a portion of the gas mixing device of FIG. 15.

The mixing pump 516B is operatively connected to the actuator, i.e., air cylinder 518B via the connecting rod 530 threaded or fastened to the plunger 528. The air cylinder 518B is identical to air cylinder 518. The air cylinder 518B is energized automatically by a controller 19 or driven manually, as described with respect to air cylinder 518. Although not shown in FIGS. 15 and 16, the valve 536 and lines 538A, 538B control pressurized air feed to either side of the land 532 to cycle the plunger 528B in the bore 526B as described with respect to plunger 528 in FIG. 10.

Both the pump body 524B and the air cylinder 518B are shown secured to a base 523B. A plunger 528B of the mixing pump 516B moves in the bore 526B of the pump body 524B. A plunger seal in the form of O-rings 529B are set in annular grooves 533B on an exterior surface of the plunger 528B and seal between the plunger 528B and the bore 526B. The O-rings 529B could be one of many compliant materials, one example of which is a perfluoroelastomer, which can be coated with a wear-resistant coating, such as teflon, to reduce wear when sliding in the bore 526B. Together, the plunger 528B and the O-rings 529B are referred to as a plunger assembly 531B. The number of O-rings 529B may vary in different embodiments. Assembly of the mixing pump 516B is relatively simple as the pump body 524B is a single component, requiring only fitting of the O-rings 529B into the grooves 533B. Although the O-rings 529B described herein provide an interference fit with the bore 526B to minimize leakage, the mixing system 511 can be configured with the vacuum device 550 as described with respect to FIG. 10 to prevent air leaks and ensure the integrity of the dose volume 76.

A method of operating a mixing system 511 is described below with respect to mixing device 512, and is equally applicable whether the mixing device 512, the mixing device 512A, or the mixing device 512B is used. When a dose volume 76 is to be tested in the RGA 70, the plunger 528 is moved to a closed position (i.e., all the way to the right in FIG. 10) and the mixing pump selection valve 522 is opened. A vacuum is then applied through the passage 68 in order to evacuate the system up to the rotary valves 66A, 66B and the mixing device 512. Once these portions of the multi-channel gas sorption device 510 are evacuated, the RGA feed valve 78 is closed. The appropriate rotary valve 66A, 66B is then actuated to connect the channel 40 to be tested to the dose volume 76 and the mixing system 511. The air cylinder 518 is then actuated to move the plunger 528 to the open position (to the far left in FIG. 10). This creates a much larger system volume for the test gas because the volume of the bore 526 of the mixing pump is sized to be many times the volume of the primary and secondary volumes. Accordingly, test gas flows out of the primary and secondary volumes connected through the rotary valve 66A or 66B and into the open volume in the pump bore 526. After the gas pressure comes to equilibrium, the air cylinder 518 is actuated to close the bore of the pump body 524 by driving the land 532 to the far right within the bore 534 of the air cylinder 518 in FIG. 9. This removes the additional volume of the pump bore 526 from the system and forces the test gas back into the primary and secondary volumes with the mixing pump selector valve 522 remaining open. The cycling of the mixing pump 516 is then repeated. Each cycle of the mixing pump 516 causes mixing to occur. The mixing pump 516 can be cycled an appropriate number of times to ensure that the gas compositions in the primary and secondary volumes are the same. The number of cycles can be predetermined by testing. After cycling is complete, the RGA feed valve 78 is opened and a dose volume 76 (i.e., a test gas sample after gas sorption by the test material) is sent to the RGA 70 for measurement. When the RGA measurements are complete for a given channel 40, this method can be repeated for the next channel to be measured.

While the best modes for carrying out the invention have been described in detail, those familiar with the art to which this invention relates will recognize various alternative designs and embodiments for practicing the invention within the scope of the appended claims.

The invention claimed is:

1. An apparatus for testing of multiple material samples comprising:
   a gas delivery control system operatively connectable to the multiple material samples and configured to provide gas to the multiple material samples;
   a gas composition measurement device;
   pressure measurement devices;
   multiple valves that are selectively openable and closable;
   a series of conduits configured to selectively connect the multiple material samples individually to the gas composition measurement device and the pressure measurement devices by operation of the valves; wherein the gas composition measurement device is downstream in the series of conduits from the multiple material samples and the pressure measurement devices;
   wherein the gas composition measurement device is operable to determine the composition of gas in the series of conduits;
   wherein the pressure measurement devices measure pressure of gas in the series of conduits for determining gas sorption by each of the multiple material samples;
   a mixing system selectively connectable to the series of conduits; and wherein the mixing system is operable to cause forced mixing of the gas within the series of conduits for each of the multiple material samples thereby increasing uniformity of gas distribution and gas composition within the series of conduits so that gas delivered from the series of conduits to the gas composition measurement device is representative of gas composition after gas sorption by the multiple material samples.

2. The apparatus of claim 1, wherein the mixing system includes a mixing pump and a mixing pump selection valve controllable to operatively connect the mixing pump and the series of conduits.

3. The apparatus of claim 2, wherein the mixing pump has:
   a pump body defining a pump bore in fluid communication with the series of conduits via the mixing pump selection valve; and
   a plunger assembly that is interference fit with the pump body in the pump bore and cyclically movable to mix the gas within the series of conduits.

4. The apparatus of claim 3, wherein the plunger assembly includes a plunger and a plunger seal around the plunger that is interference fit to the pump body in the pump bore; and further comprising:
   an actuator operatively connected to the plunger to cyclically move the plunger assembly back and forth in the pump bore.

5. The apparatus of claim 4, wherein the plunger seal has a series of ridges that are in contact with the pump body in the pump bore and are configured to prevent leakage of the gas from the series of conduits while permitting the plunger seal to slide against the pump body.

6. The apparatus of claim 4, wherein the plunger seal is a series of O-rings.

7. The apparatus of claim 4, further comprising:
   a vacuum device in fluid communication with the pump body and configured to prevent air flow past the seal into the series of conduits.

8. The apparatus of claim 7, wherein the vacuum device includes a vacuum enclosure that encloses both the mixing pump and the plunger assembly.

9. The apparatus of claim 8, wherein the vacuum device includes a passage through the plunger in fluid communication with the plunger seal between the plunger seal and the pump body.

10. The apparatus of claim 1
    wherein the series of conduits and multiple valves define, for each of the material samples, a primary volume in fluid communication with the material sample, a secondary volume in selective communication with the primary volume, and a dose volume deliverable to the gas composition measurement device and in selective communication with the secondary volume;
    wherein each of the pressure measurement devices is operatively connected to the secondary volume of a respective different one of the multiple material samples and operable to measure pressure of gas in the secondary volume for determining gas sorption by the respective different one of the multiple material samples.

11. The apparatus of claim 1,
wherein the gas delivery control system includes a delivery manifold with a common gas flow outlet in selective fluid communication with different ones of the multiple material samples through multiple gas flow channels of the series of conduits;
and further comprising:
a pressure reduction system selectively operatively connecting any selected one of the multiple gas flow channels with the gas composition measurement device and configured to reduce gas pressure of gas provided from said selected one of the multiple gas flow channels to the gas composition measurement device.

12. The apparatus of claim 1,
wherein opening and closing of the multiple valves is at least partially dependent upon a pressure measurement of said at least one pressure measurement device such that the test gas provided to the multiple material samples is at a predetermined pressure or within a predetermined pressure range.

13. The apparatus of claim 12, wherein the pressure reduction system includes a pressure vessel defining an additional volume; and
wherein flow of the test gas to the one additional volume reduces pressure of the test gas to below a predetermined level; wherein the predetermined level is based on an operating parameter of the gas composition measurement device.

14. The apparatus of claim 4, wherein the actuator is an air cylinder with a cylinder bore; wherein the plunger assembly includes a land fit within the cylinder bore and a connecting rod that connects the land and the plunger;
wherein the air cylinder includes a selector valve controllable to alternately permit pressurized air to a first portion of the cylinder bore on one side of the land and to a second portion of the cylinder bore on an opposite side of the land to cause the plunger to move back and forth in the pump bore.

15. The apparatus of claim 14, further comprising air lines connecting the selector valve to the first and second portions of cylinder bore; and
wherein the airlines each have a restrictive orifice.

16. The apparatus of claim 11, wherein the pressure reduction system includes a pressure vessel defining an additional volume; and
wherein flow of the test gas to the additional volume reduces pressure of the test gas to below a predetermined level; wherein the predetermined level is based on an operating parameter of the gas composition measurement device.

17. The apparatus of claim 16, wherein the additional volume is a first additional volume; and further comprising:
a second pressure vessel defining a second additional volume in selective communication with the first additional volume to provide a total additional volume equal to both the first and the second additional volumes.

18. The apparatus of claim 2, wherein the mixing pump has:
a pump body defining a pump bore in fluid communication with the series of conduits via the mixing pump selection valve;
a plunger assembly that is cyclically movable in the pump bore to mix the gas within the series of conduits;
wherein the plunger assembly includes a plunger and a plunger seal around the plunger; wherein the plunger seal fits to the pump body in the pump bore; and
wherein the plunger is configured to permit a vacuum to be applied through the plunger to the plunger seal.

19. The apparatus of claim 18, wherein the plunger seal has a series of ridges that are in contact with the pump body in the pump bore and are configured to prevent leakage of the gas from the series of conduits while permitting the plunger seal to slide against the pump body.

* * * * *